US010188367B2

(12) United States Patent
Takagi

(10) Patent No.: US 10,188,367 B2
(45) Date of Patent: Jan. 29, 2019

(54) ULTRASOUND DIAGNOSTIC DEVICE, ULTRASOUND IMAGE PROCESSING METHOD, AND NON-TRANSITORY COMPUTER-READABLE RECORDING MEDIUM

(71) Applicant: KONICA MINOLTA, INC., Chiyoda-ku, Tokyo (JP)

(72) Inventor: Kazuya Takagi, Machida (JP)

(73) Assignee: KONICA MINOLTA, INC., Tokyo (JP)

(*) Notice: Subject to any disclaimer, the term of this patent is extended or adjusted under 35 U.S.C. 154(b) by 725 days.

(21) Appl. No.: 14/566,331

(22) Filed: Dec. 10, 2014

(65) Prior Publication Data
US 2015/0157296 A1    Jun. 11, 2015

(30) Foreign Application Priority Data

Dec. 11, 2013 (JP) .................................. 2013-256062
Dec. 8, 2014 (JP) .................................. 2014-247924

(51) Int. Cl.
A61B 8/08    (2006.01)
A61B 17/34   (2006.01)
(Continued)

(52) U.S. Cl.
CPC .............. A61B 8/0841 (2013.01); A61B 8/08 (2013.01); A61B 8/485 (2013.01);
(Continued)

(58) Field of Classification Search
CPC ......... A61B 8/08; A61B 8/485; A61B 8/0841; A61B 2034/2063; A61B 2090/378; A61B 2017/3413
See application file for complete search history.

(56) References Cited

U.S. PATENT DOCUMENTS 6,216,029 B1 * 4/2001 Paltieli ................. A61B 8/0833
                                                    600/411
9,226,729 B2 * 1/2016 Tashiro ................. A61B 8/0841
(Continued)

FOREIGN PATENT DOCUMENTS

JP    2000107178 A    4/2000
JP    2001269339 A    10/2001
(Continued)

OTHER PUBLICATIONS

Extended European Search Report dated Apr. 9, 2015, issued in counterpart European Application No. 14197341.2.
(Continued)

Primary Examiner — Angela M Hoffa
(74) Attorney, Agent, or Firm — Holtz, Holtz & Volek PC

(57) ABSTRACT

Ultrasound image processing method and ultrasound diagnostic device using the method, the method including: acquiring frame signals generated at different time points; generating, by using the frame signals, a first motion map composed of pixel areas each having a motion, the motion indicating an inter-frame signal change and calculated from corresponding pixel areas of the frame signals; holding a second motion map and creating a third motion map by performing a calculation using motions in the first and second motion maps; and adding emphasis to a frame signal by using the third motion map and generating an ultrasound image from the frame signal. In the method, after the calculation using motions, the third motion map is held in place of the second motion map.

21 Claims, 19 Drawing Sheets

(51) Int. Cl.
*A61B 90/00* (2016.01)
*A61B 34/20* (2016.01)
(52) U.S. Cl.
CPC ............... *A61B 2017/3413* (2013.01); *A61B 2034/2063* (2016.02); *A61B 2090/378* (2016.02)

(56) References Cited

U.S. PATENT DOCUMENTS

| | | | | |
|---|---|---|---|---|
| 9,326,749 | B2* | 5/2016 | Okamura | A61B 8/0841 |
| 9,326,750 | B2* | 5/2016 | Takeda | A61B 8/0841 |
| 9,706,978 | B2* | 7/2017 | Baek | A61B 8/5207 |
| 2007/0016035 | A1 | 1/2007 | Hashimoto | |
| 2009/0225827 | A1 | 9/2009 | Sang et al. | |
| 2009/0288011 | A1* | 11/2009 | Piran | G08B 13/19693 715/720 |
| 2011/0125018 | A1 | 5/2011 | Shin et al. | |
| 2011/0201931 | A1* | 8/2011 | Palmeri | A61B 8/0841 600/440 |
| 2011/0249878 | A1* | 10/2011 | Pagoulatos | A61B 8/0841 382/131 |
| 2011/0317897 | A1 | 12/2011 | Narasimhamurthy et al. | |
| 2012/0078103 | A1 | 3/2012 | Tashiro et al. | |
| 2012/0108974 | A1* | 5/2012 | Katou | A61B 8/461 600/445 |
| 2012/0253181 | A1* | 10/2012 | Okamura | A61B 8/0841 600/424 |
| 2013/0274608 | A1* | 10/2013 | Takeda | A61B 8/0841 600/461 |
| 2014/0128728 | A1* | 5/2014 | Baek | A61B 8/5207 600/424 |
| 2014/0148689 | A1* | 5/2014 | Lee | G06T 7/73 600/424 |
| 2014/0187942 | A1* | 7/2014 | Wang | A61B 8/0841 600/439 |
| 2014/0323854 | A1* | 10/2014 | Takeda | G06T 7/73 600/424 |
| 2014/0362114 | A1* | 12/2014 | Li | A61B 8/0841 345/633 |
| 2015/0164482 | A1* | 6/2015 | Toji | A61B 8/5276 600/443 |
| 2015/0223776 | A1* | 8/2015 | Ohuchi | A61B 8/0841 600/424 |
| 2015/0245819 | A1* | 9/2015 | Yoshiara | A61B 8/06 600/424 |
| 2015/0289839 | A1* | 10/2015 | Saito | A61B 8/463 600/424 |
| 2015/0320397 | A1* | 11/2015 | Takagi | A61B 8/0841 600/424 |
| 2015/0320401 | A1* | 11/2015 | Takagi | A61B 8/5276 600/424 |
| 2015/0342561 | A1* | 12/2015 | Takeda | A61B 8/0841 600/424 |
| 2016/0000400 | A1* | 1/2016 | Korsten | A61B 8/0833 600/439 |
| 2016/0135781 | A1* | 5/2016 | Okamura | A61B 8/0841 600/424 |
| 2016/0199024 | A1* | 7/2016 | Takeda | A61B 8/0841 600/424 |
| 2016/0199025 | A1* | 7/2016 | Takeda | A61B 8/0841 600/424 |
| 2016/0317118 | A1* | 11/2016 | Parthasarathy | A61B 8/0841 |
| 2017/0049420 | A1* | 2/2017 | Shikama | A61B 8/5276 |
| 2017/0143294 | A1* | 5/2017 | Tashiro | A61B 8/0841 |

FOREIGN PATENT DOCUMENTS

| | | |
|---|---|---|
| JP | 4381344 B2 | 12/2009 |
| JP | 2012120747 A | 6/2012 |

OTHER PUBLICATIONS

Chinese Office Action (and English translation thereof) dated Aug. 10, 2016, issued in counterpart Chinese Application No. 201410766747.8.

European Office Action dated Aug. 23, 2016, issued in counterpart European Application No. 14197341.2.

Chinese Office Action (and English translation thereof) dated Mar. 23, 2017 issued in counterpart Chinese Application No. CN201410766747.8.

European Office Action dated Sep. 19, 2017, issued in counterpart European Application No. 14197341.2.

\* cited by examiner

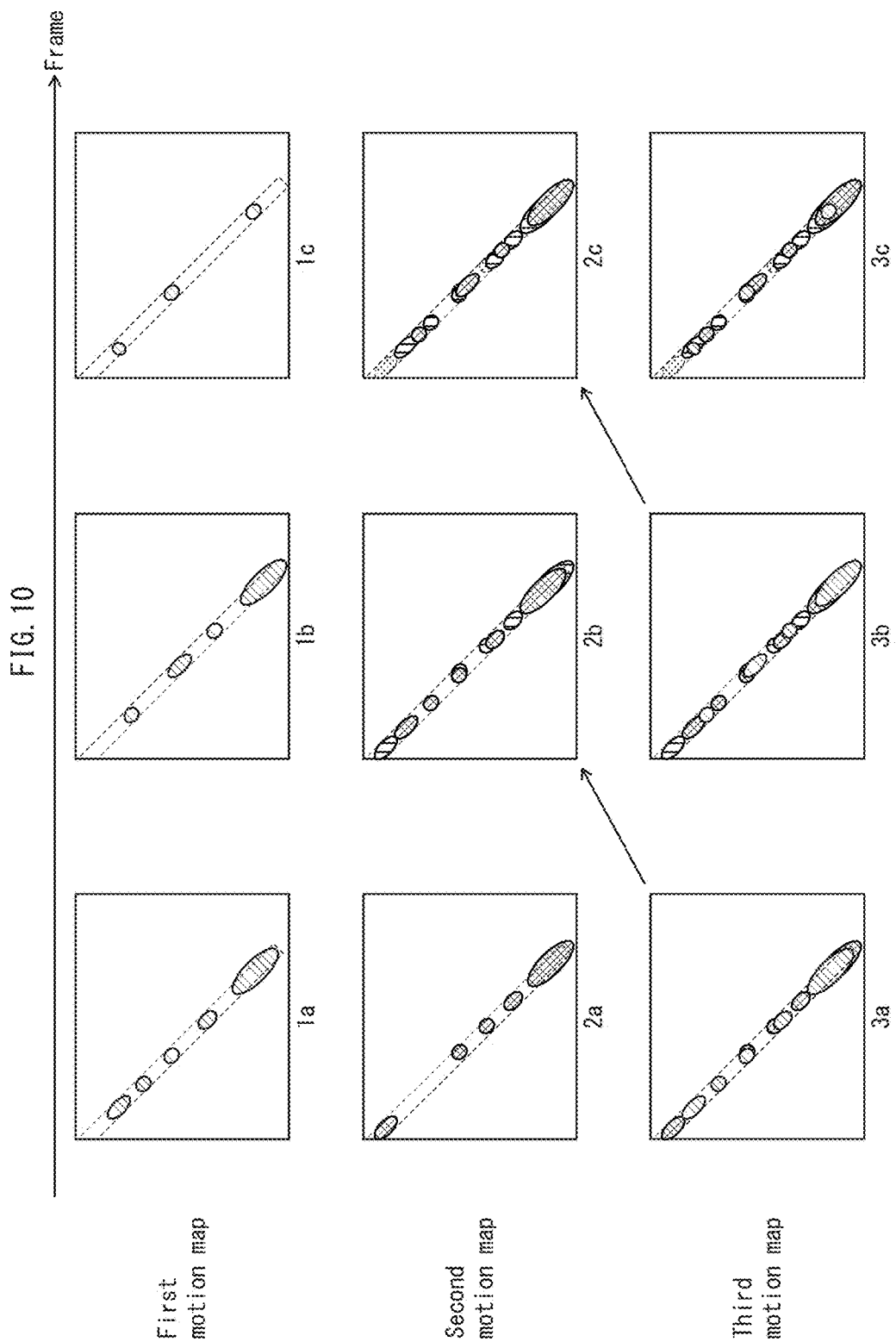

ULTRASOUND DIAGNOSTIC DEVICE, ULTRASOUND IMAGE PROCESSING METHOD, AND NON-TRANSITORY COMPUTER-READABLE RECORDING MEDIUM

This application is based on Japanese Patent Application No. 2013-256062 filed on Dec. 11, 2013, and Japanese Patent Application No. 2014-247924 filed on Dec. 8, 2014, the disclosure therein, including disclosure in the claims, the specification, the drawings, and the abstract, is hereby incorporated by reference.

BACKGROUND OF THE DISCLOSURE (1) Technical Field

The present disclosure relates to an ultrasound diagnostic device and an ultrasound image processing method that visualize a puncture needle with enhanced perceptibility.

(2) Description of the Related Art

In recent years, a medical test commonly called biopsy is being performed. In biopsy, a puncture needle is inserted into a living subject, such as the body of a patient, and tissue samples and/or body fluid samples are removed for examination. Further, anesthesiology, which is practiced by anesthesiologists in intensive care units, pain clinics, etc., also involves the use of puncture needles. In such anesthesiology, medical practitioners perform puncture needle insertion while checking the position of the puncture needle in the examination subject by viewing ultrasound images showing the inside of the examination subject, which are obtained by using an ultrasound probe provided to an ultrasound diagnostic device. Here, in puncture needle insertion, it is necessary for medical practitioners to be able to check the position of the puncture needle in the examination subject, particularly the position of the tip of the puncture needle, on an ultrasound diagnostic device monitor.

In particular, in cases where an angle between an ultrasound beam and a puncture needle is relatively small, such as when a puncture needle is inserted into an examination subject with a sharp angle between the puncture needle and the examination subject surface, ultrasound waves reflected from the puncture needle and received by the ultrasound probe are weak, and thus, the puncture needle is not sufficiently visibly perceptible. Thus, much consideration has been made related to a technology for improving the visual perceptibility of puncture needles.

Japanese Patent No. 4381344 discloses one example of such technology. Japanese Patent No. 4381344 discloses a method of changing the transmission direction of the ultrasound beam so as to enlarge the angle between the ultrasound beam and the puncture needle, to avoid having to insert the puncture needle into the examination subject with a relatively small angle between the puncture needle and the examination subject surface. Japanese Patent Application Publications No. 2000-107178, No. 2001-269339, and No. 2012-120747 disclose another example of such technology. Japanese Patent Application Publications No. 2000-107178, No. 2001-269339, and No. 2012-120747 disclose a method of adding visual emphasis to portions differing between frames, where such portions of difference are regarded as image areas indicating signal changes corresponding to the movement of the puncture needle.

SUMMARY

Problems to be Solved

However, when applying the method of changing the transmission direction of the ultrasound beam, areas of the examination subject that cannot be visualized in ultrasound images increase. Further, when applying the method of adding visual emphasis to portions differing between frames, motions detected tend to be sparsely distributed, and thus, the emphasis added to an image based on such motions may not be sufficient.

In view of such technical problems, the present disclosure provides an ultrasound diagnostic device and an ultrasound image processing method that are user-friendly and that visualize a target object (e.g., a puncture needle) located inside an imaging subject (e.g., an examination subject) with high perceptibility.

Means for Solving the Problems

One aspect of the present disclosure is an ultrasound diagnostic device that transmits ultrasound waves towards a subject via an ultrasound probe and acquires a frame signal by receiving ultrasound waves reflected by the subject via the ultrasound probe, the ultrasound diagnostic device including an ultrasound image processing circuit that adds emphasis to the frame signal and generates an ultrasound image in which the subject appears from the frame signal. In the ultrasound diagnostic device, the ultrasound image processing circuit includes: a signal acquirer that acquires a plurality of frame signals generated at different time points; a map generator that generates, by using the frame signals, a first motion map composed of a plurality of pixel areas each having a motion, the motion indicating an inter-frame signal change and calculated from corresponding pixel areas of the frame signals; a map calculator that holds a second motion map and creates a third motion map by performing a calculation using motions in the first motion map and the second motion map; and an emphasis adder that adds emphasis to at least one of the frame signals by using the third motion map and generates an ultrasound image from said at least one of the frame signals. In the ultrasound diagnostic device, after the calculation using motions, the map calculator holds the third motion map in place of the second motion map.

BRIEF DESCRIPTION OF THE DRAWINGS

These and the other objects, advantages and features of the present disclosure will become apparent from the following description thereof taken in conjunction with the accompanying drawings which illustrate a specific embodiment of the present disclosure.

In the drawings:

FIG. 10 is a schematic diagram illustrating a motion map update performed by a motion map computation unit 65;

DESCRIPTION OF THE PREFERRED EMBODIMENTS

«How Inventors Arrived at Present Disclosure»

Conventionally, consideration has been made of technology for improving visual perceptibility of puncture needles, as described in the following.

Figure 18A:
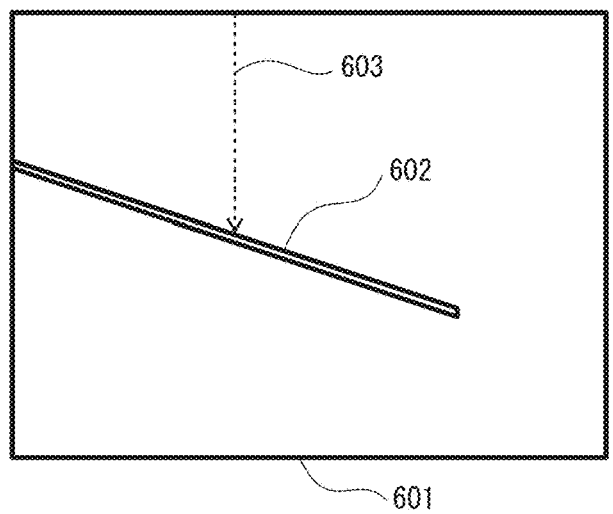
FIG. 18A illustrates one example of a B-mode image of puncture needle insertion.
Figure 18B:
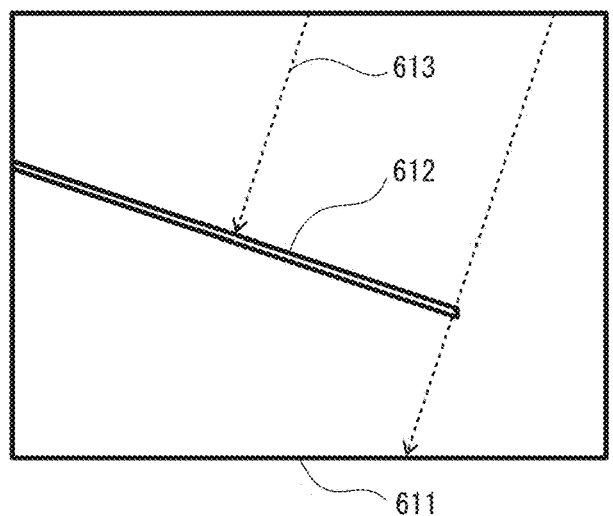
FIG. 18B illustrates one example of a B-mode image of puncture needle insertion acquired by changing ultrasound beam transmission direction.
Figure 18C:
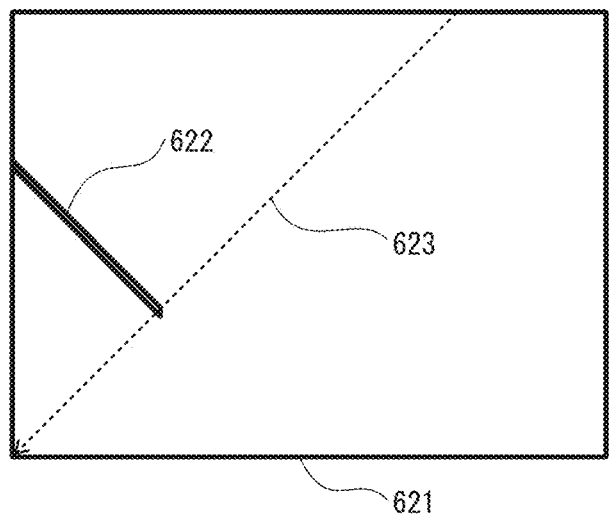
FIG. 18C illustrates another example of a B-mode image of puncture needle insertion acquired by changing ultrasound beam transmission direction, each of FIGS. 18A through 18C illustrating a B-mode image with indication of ultrasound beam transmission direction overlaid thereon.

One example of such a technology is a method of enlarging the angle between an ultrasound beam and a puncture needle. One simple form of such a method is to perform insertion of a puncture needle 602 with the puncture needle 602 almost parallel with skin surface as in ultrasound image 601 illustrated in FIG. 18A, whereby the angle between the puncture needle 602 and an ultrasound beam 603 can be enlarged. (Note that each of FIGS. 18A through 18C illustrates a B-mode image with indication of ultrasound beam transmission direction overlaid thereon.) However, when inserting the puncture needle 602 at such an angle, the distance that the puncture needle 602 travels between the skin surface and the target body tissue of the examination subject increases. This results in much damage being made to the examination subject tissue. In view of such a problem, Japanese Patent No. 4381344 discloses a technology of transmitting an ultrasound beam 613 diagonal to the skin surface and not perpendicular to the skin surface, as in ultrasound image 611 illustrated in FIG. 18B. This allows ensuring a large angle between a puncture needle 612 and the ultrasound beam 613, even when the puncture needle 612 is inserted slightly diagonal to the skin surface. However, when employing this technology and inserting a puncture needle 622 close to perpendicular to the skin surface as in ultrasound image 621 illustrated in FIG. 18C, a necessity arises of transmitting an ultrasound beam 623 close to parallel with the skin surface. This results in an increase in non-visualized areas of the examination subject. Further, it should be noted that when using an ultrasound probe having a one-dimensional array of elements (e.g., a linear type ultrasound probe or a convex type ultrasound probe) and not an ultrasound probe having a two-dimensional array of elements (e.g., a matrix type ultrasound probe), ultrasound beam transmission direction cannot be controlled in a direction perpendicular to the element arrangement direction. Due to this, the above-described technology of changing the transmission direction of an ultrasound beam is not effective, particularly when used in combination with an ultrasound probe having a one-dimensional array of elements and when there is a need to insert a puncture needle in a direction perpendicular to the element arrangement direction.

Figure 19:
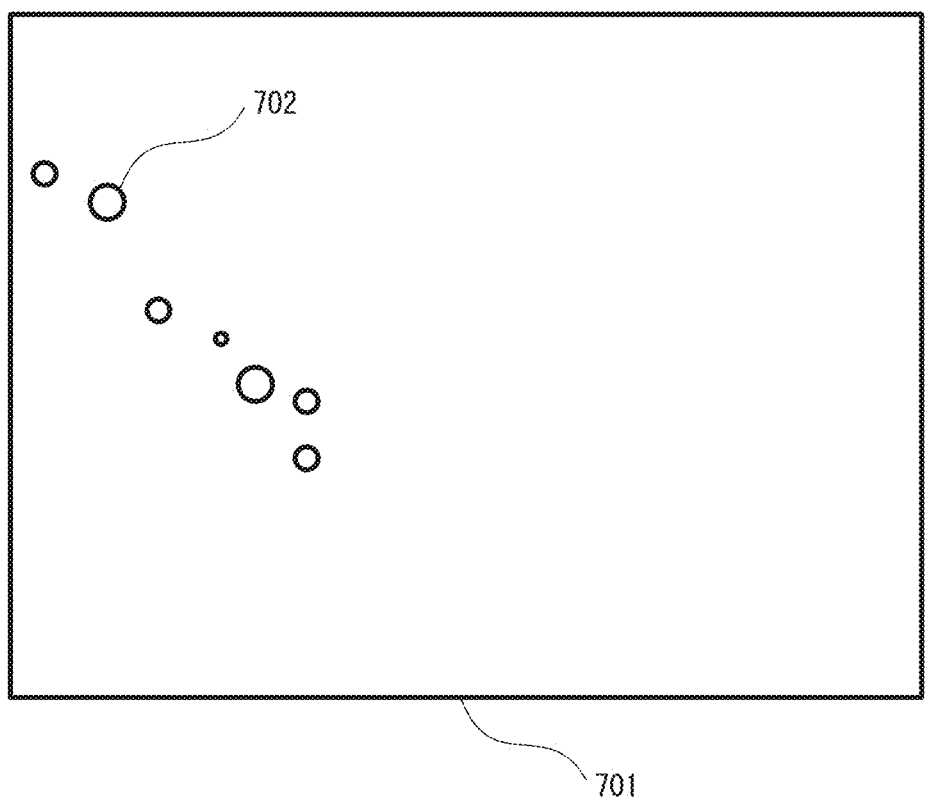
FIG. 19 is a schematic diagram illustrating one example of a distribution of motions between two successive B-mode image frames.

Another example of a technology for improving visual perceptibility of puncture needles is adding emphasis to portions differing between frames, regarding such image portions as image areas indicating signal changes corresponding to the movement of the puncture needle. Japanese Patent Application Publications No. 2000-107178, No. 2001-269339, and No. 2012-120747 disclose technologies of adding emphasis to inter-frame differences in the form of coloring. However, when employing such technology, the inter-frame differences (motions) detected tend to be sparsely distributed, as illustrated in motion map 701 illustrated in FIG. 19, due to successive frames being captured at close time points. This results in the emphasis added to the puncture needle being insufficient. Further, another problem with such a technology is that emphasis is not added when the puncture needle does not move. In addition, yet another problem with such a technology is that emphasis is added to all image areas when the ultrasound probe moves, due to inter-frame differences being detected at all areas.

In view of such technical problems, the present inventors considered enabling visualizing puncture needles with high perceptibility by adding emphasis to signal changes corresponding to the movement of a puncture needle at higher spatial density and while causing the emphasis added to be visualized over time. It is through such consideration that the present inventors arrived at the ultrasound diagnostic devices, the ultrasound image processing methods, and the ultrasound image processing programs pertaining to the embodiments and the modifications.

The following describes in detail the ultrasound diagnostic devices, the ultrasound image processing methods, and the ultrasound image processing programs pertaining to the embodiments and the modifications, with reference to the accompanying drawings.

«Overview of Aspects»

One aspect of the present disclosure is an ultrasound diagnostic device that transmits ultrasound waves towards a subject via an ultrasound probe and acquires a frame signal by receiving ultrasound waves reflected by the subject via the ultrasound probe, the ultrasound diagnostic device including an ultrasound image processing circuit that adds emphasis to the frame signal and generates an ultrasound image in which the subject appears from the frame signal. In the ultrasound diagnostic device, the ultrasound image processing circuit includes: a signal acquirer that acquires a plurality of frame signals generated at different time points; a map generator that generates, by using the frame signals, a first motion map composed of a plurality of pixel areas each having a motion, the motion indicating an inter-frame signal change and calculated from corresponding pixel areas of the frame signals; a map calculator that holds a second motion map and creates a third motion map by performing a calculation using motions in the first motion map and the second motion map; and an emphasis adder that adds emphasis to at least one of the frame signals by using the third motion map and generates an ultrasound image from said at least one of the frame signals. In the ultrasound diagnostic device, after the calculation using motions, the map calculator holds the third motion map in place of the second motion map.

In the ultrasound diagnostic device pertaining to one aspect of the present disclosure, in the creation of the third motion map, the map calculator may set, as a motion for each pixel area of the third motion map, a greater one of (i) a value obtained by attenuating a motion of a corresponding pixel area in the second motion map based on a predetermined attenuation factor and (ii) a motion of a corresponding pixel in the first motion map.

In the ultrasound diagnostic device pertaining to one aspect of the present disclosure, the predetermined attenuation factor may be set according to a frame rate of the frame signals.

The ultrasound diagnostic device pertaining to one aspect of the present disclosure may further include a controller for receiving input of the predetermined attenuation factor.

In the ultrasound diagnostic device pertaining to one aspect of the present disclosure, the calculation using motions may be alpha-blending the second motion map and the first motion map.

In the ultrasound diagnostic device pertaining to one aspect of the present disclosure, an alpha value used in the alpha blending may be set according to a frame rate of the frame signals.

The ultrasound diagnostic device pertaining to one aspect of the present disclosure may further include a controller for receiving input of an alpha value to be used in the alpha blending.

In the ultrasound diagnostic device pertaining to one aspect of the present disclosure, the ultrasound image processing circuit may further include a weight provider that provides a weight to each motion in the first motion map based on a luminance value of a corresponding pixel area of one or more of the frame signals, and outputs the first motion map, whose motions have been weighted, to the map calculator.

In the ultrasound diagnostic device pertaining to one aspect of the present disclosure, the weight provider, when the luminance value of the corresponding pixel area is lower than a predetermined value, may provide a weight to the motion in the first motion map by using zero as a weighting coefficient, so that after weighting by the weighting unit, among the pixel areas in the first motion map, only one or more pixel areas corresponding to a puncture needle have motions, the one or more pixel areas corresponding to one or more pixel areas of said at least one of the frame signals having luminance values greater than the predetermined value.

In the ultrasound diagnostic device pertaining to one aspect of the present disclosure, the ultrasound image processing circuit may further include an emphasis adjuster that, when a movement of the ultrasound probe in a direction along a surface of the subject occurs, detects a signal change indicating the movement of the ultrasound probe, adjusts motions in the third motion map based on the signal change indicating the movement of the ultrasound probe by using a non-increasing function, and outputs the third motion map, whose motions have been adjusted, to the emphasis adder.

In the ultrasound diagnostic device pertaining to one aspect of the present disclosure, the emphasis adjuster may calculate the signal change indicating the movement of the ultrasound probe by using the first motion map.

In the ultrasound diagnostic device pertaining to one aspect of the present disclosure, the ultrasound probe may include a sensor that detects either a position of the ultrasound probe or an orientation of the ultrasound probe, and the emphasis adjuster may use a value output by the sensor as the signal change indicating the movement of the ultrasound probe.

In the ultrasound diagnostic device pertaining to one aspect of the present disclosure, the ultrasound image processing circuit may further include an emphasis adjuster that, when a movement of the ultrasound probe in a direction along a surface of the subject occurs, detects a signal change indicating the movement of the ultrasound probe, adjusts the motions in the first motion map based on the signal change indicating the movement of the ultrasound probe by using a non-increasing function, and outputs the first motion map, whose motions have been adjusted, to the map calculator.

In the ultrasound diagnostic device pertaining to one aspect of the present disclosure, the emphasis adjuster may calculate the signal change indicating the movement of the ultrasound probe by using the first motion map.

In the ultrasound diagnostic device pertaining to one aspect of the present disclosure, the ultrasound probe may include a sensor that detects either a position of the ultrasound probe or an orientation of the ultrasound probe, and the emphasis adjuster may use a value output by the sensor as the signal change indicating the movement of the ultrasound probe.

In the ultrasound diagnostic device pertaining to one aspect of the present disclosure, the emphasis adder may change a pixel value of a pixel area of said at least one of the frame signals based on a motion at a corresponding pixel area in the third motion map by using a non-decreasing function.

In the ultrasound diagnostic device pertaining to one aspect of the present disclosure, the emphasis adder may add emphasis to one or more pixel areas of said at least one of the frame signals corresponding to one or more pixel areas in the third motion map having a motion greater than a predetermined threshold value.

In the ultrasound diagnostic device pertaining to one aspect of the present disclosure, the emphasis adder may add emphasis to one or more pixel areas of said at least one of the frame signals corresponding to one or more pixel areas in the third motion map having a motion greater than a predetermined threshold value, the adding of emphasis performed by overlaying an icon and changing a pixel value.

In the ultrasound diagnostic device pertaining to one aspect of the present disclosure, the emphasis adder may add emphasis to one pixel area of said at least one of the frame signals corresponding to one pixel area in the third motion map having a greatest motion, the adding of emphasis performed by overlaying an icon and changing a pixel value.

The ultrasound diagnostic device pertaining to one aspect of the present disclosure may further include a storage medium for storing the second motion map, and the map calculator may hold the second motion map by writing the second motion map to the storage medium.

One aspect of the present disclosure is an ultrasound image processing method for adding emphasis to a frame signal and generating an ultrasound image from the frame signal, the frame signal acquired by receiving ultrasound waves reflected by a subject via an ultrasound probe when the ultrasound probe transmits ultrasound waves towards the subject, the ultrasound image processing method including: acquiring a plurality of frame signals generated at different time points; generating, by using the frame signals, a first motion map composed of a plurality of pixel areas each having a motion, the motion indicating an inter-frame signal change and calculated from corresponding pixel areas of the frame signals; holding a second motion map and creating a third motion map by performing a calculation using motions in the first motion map and the second motion map; and adding emphasis to at least one of the frame signals by using the third motion map and generating an ultrasound image from said at least one of the frame signals. In the ultrasound image processing method pertaining to one aspect of the present disclosure, after the calculation using motions, the third motion map is held in place of the second motion map.

One aspect of the present invention is a non-transitory computer-readable recording medium storing thereon a program that causes a processor of an ultrasound diagnostic device to execute image processing for adding emphasis to frame signals and generating ultrasound images from the frame signals, the ultrasound diagnostic device acquiring the frame signals by receiving ultrasound waves reflected by a subject via an ultrasound probe when the ultrasound probe transmits ultrasound waves towards the subject, the image processing including: acquiring a plurality of frame signals generated at different time points; generating, by using the frame signals, a first motion map composed of a plurality of pixel areas each having a motion, the motion indicating an inter-frame signal change and calculated from corresponding pixel areas of the frame signals; holding a second motion map and creating a third motion map by performing a calculation using motions in the first motion map and the second motion map; and adding emphasis to at least one of the frame signals by using the third motion map and generating an ultrasound image from said at least one of the frame signals. In the non-transitory computer-readable recording medium pertaining to one aspect of the present disclosure, after the calculation using motions, the third motion map is held in place of the second motion map.

<Embodiment 1>

The following describes an ultrasound diagnostic device pertaining to embodiment 1, with reference to the accompanying drawings.

<Structure>

<Ultrasound Diagnostic Device 100>

Figure 1:
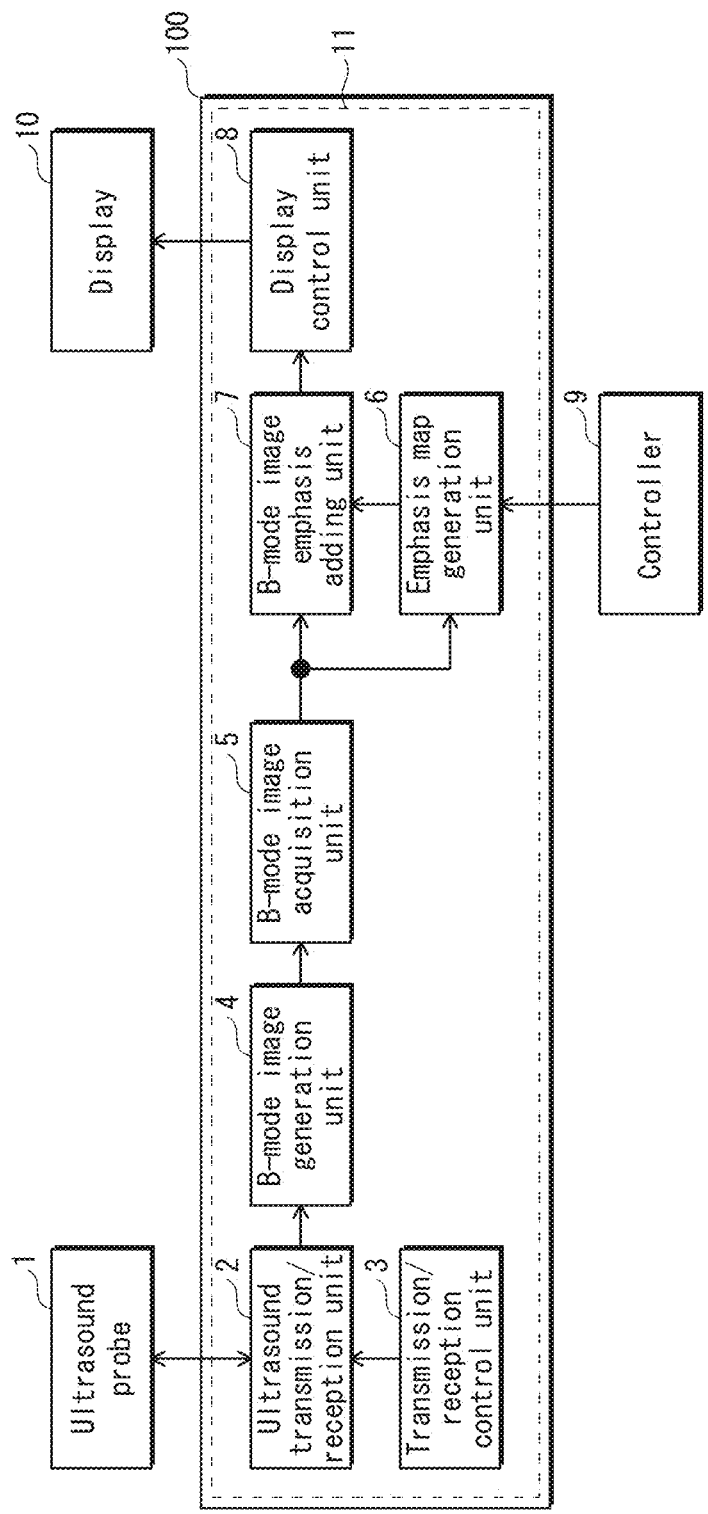
FIG. 1 is a block diagram illustrating an ultrasound diagnostic device 100 pertaining to embodiment 1.

FIG. 1 is a block diagram illustrating the structure of an ultrasound diagnostic device 100 pertaining to embodiment 1. The ultrasound diagnostic device 100 includes an ultrasound image processing circuit 11. The ultrasound image processing circuit 11 includes: an ultrasound transmission/reception unit 2; a transmission/reception control unit 3; a B-mode image generation unit 4; a B-mode image acquisition unit 5; an emphasis map generation unit 6; a B-mode image emphasis adding unit 7; and a display control unit 8. An ultrasound probe 1 is connectable to the ultrasound transmission/reception unit 2. A controller 9 is connectable to the emphasis map generation unit 6 via an undepicted control unit. A display 10 is connectable to the display control unit 8. FIG. 1 illustrates a state of the ultrasound diagnostic device 100 where the ultrasound probe 1, the controller 9, and the display 10 are connected thereto.

The ultrasound probe 1, for example, includes a plurality of transducers (undepicted) arranged to form a line extending in one direction. The direction along which the transducers are disposed is referred to in the following as a transducer arrangement direction. Each transducer is made of lead zirconate titanate (PZT), for example. The ultrasound probe 1 converts pulsed electric signals (referred to in the following as ultrasound transmission signals) generated by the ultrasound transmission/reception unit 2 into pulsed ultrasound waves. The ultrasound probe 1, or more specifically, a transducer-side outer surface of the ultrasound probe 1, is put in contact with a surface of an imaging subject. In this state, the ultrasound probe 1 transmits an ultrasound beam toward a measurement target. Here, the imaging subject may be an examination subject, and the surface of the imaging subject may be a skin surface of the examination subject. Further, the ultrasound beam is composed of the ultrasound waves emitted from the transducers. The ultrasound probe 1 receives reflected ultrasound waves. The reflected ultrasound waves are ultrasound waves that are reflected from the imaging subject. The transducers in the ultrasound probe 1 converts the reflected ultrasound waves into electric signals (referred to in the following as ultrasound reception signals). The ultrasound probe 1 supplies the ultrasound reception signals to the ultrasound transmission/reception unit 2.

The ultrasound transmission/reception unit 2 performs transmission based on a transmission control signal that the transmission/reception control unit 3 transmits thereto. The ultrasound transmission/reception unit 2, when executing the transmission, supplies the ultrasound probe 1 with the pulsed ultrasound transmission signals, which cause the ultrasound probe 1 to transmit the ultrasound beam. More specifically, the ultrasound transmission/reception unit 2 includes circuits such as: a clock generation circuit; a pulse generation circuit; and a delay circuit. The clock generation circuit generates a clock signal used for determining transmission timing of the ultrasound beam. The pulse generation circuit generates a pulsed signal for driving the transducers. The delay circuit sets a delay time with respect to each transducer, and delays the transmission of the ultrasound waves from the transducers by the respective delay times. Thus, the delay circuit realizes beam-focusing, beam-steering, etc., of the ultrasound beam.

Further, the ultrasound transmission/reception unit 2 acquires the ultrasound reception signals from the ultrasound probe 1. As already described above, the ultrasound reception signals are yielded from the reflected ultrasound waves. The ultrasound transmission/reception unit 2 amplifies the ultrasound reception signals, and performs A/D conversion with respect to the amplified signals to obtain RF signals. Further, the ultrasound transmission/reception unit 2 performs delay-and-sum on the RF signals to generate a plurality of echo signals. The delay-and-sum is performed by using a reception control signal. As discussed in detail in the following, the echo signals so generated are signals having signal components corresponding to continuous depth areas. Further, the ultrasound transmission/reception unit 2 performs reception. The ultrasound transmission/reception unit 2, when executing the reception, outputs the echo signals to the B-mode image generation unit 4 in chronological order, in the order from those obtained upstream in the sub-scanning direction to those obtained downstream in the sub-scanning direction.

For example, the RF signals are signals along the direction in which the ultrasound waves travel, which is perpendicular to the transducer arrangement direction. Each of the RF signals is a digital signal yielded by A/D-converting an electrical signal that is yielded by converting an amplitude of a reflected ultrasound wave.

Each of the echo signals is data having components corresponding to continuous depth direction areas. The echo signals compose the delay-and-summed RF signals. Here, the depth direction is the direction in which transmitted ultrasound waves travel from the body surface of the examination subject towards the inside of the examination subject's body. The echo signals compose one frame. Thus, one frame is composed of a plurality of signals along the direction in which ultrasound waves are transmitted, which is perpendicular to the transducer arrangement direction. Note that in the present disclosure, a set of echo signals acquired through a single ultrasound scan is referred to as a frame echo signal. Further, in the present disclosure, the term "frame" refers to a unit of signals necessary in order to construct one cross-sectional image.

The ultrasound transmission/reception unit 2 performs transmission and reception in this order repeatedly.

The transmission/reception control unit 3 generates the transmission control signal and the reception control signal, and outputs such signals to the ultrasound transmission/reception unit 2. Note that in the present embodiment, the transmission control signal includes information indicating transmission timing, and the reception control signals include information indicating reception timing.

The B-mode image generation unit 4 converts each one of the echo signals composing one frame into a luminance signal having a luminance value corresponding to the intensity of the echo signal. Further, the B-mode image generation unit 4 performs coordinate conversion on the luminance signals to acquire a signal based on an orthogonal coordinate system. Thus, the B-mode image generation unit 4 generates a B-mode image signal. The B-mode image generation unit 4 generates a B-mode image for each frame, and outputs the B-mode images so generated to the B-mode image acquisition unit 5. In specific, the B-mode image generation unit 4 generates a B-mode image signal by performing processing such as envelope detection and logarithmic compression on echo signals composing one frame (i.e., the frame echo signal) to convert the echo signals into luminance signals, and performing coordinate conversion on the luminance signals to obtain a signal based on an orthogonal coordinate system. As such, the B-mode image signal carries luminance values indicating the intensity of the ultrasound reception signals. The B-mode image generation unit 4 transmits the B-mode image so generated to the B-mode image acquisition unit 5 each time an ultrasound scan is performed.

The B-mode image acquisition unit 5 is a buffer that stores the B-mode image signal that is transmitted each time an ultrasound scan is performed. For example, the B-mode image acquisition unit 5 is implemented by using a RAM, a flash memory, or a hard disk drive.

Further, in the present disclosure, the term reception signal (ultrasound reception signal) is used to refer to one B-mode image signal or a frame echo signal (i.e., echo signal composing one frame), based on which one B-mode image signal is generated.

The emphasis map generation unit 6 receives, as input, a B-mode image signal stored in the B-mode image acquisition unit 5 and parameters input via the controller 9. The parameters include "intensity", "image lag", and "emphasize with color". The emphasis map generation unit 6 generates an emphasis map, and outputs the emphasis map to the B-mode image emphasis adding unit 7. The emphasis map is a map used when adding emphasis to motions corresponding to puncture needle insertion. In specific, the emphasis map is a map indicating the amount of emphasis to be added to pixel areas (i.e., pixels) of the B-mode image signal. Details of the specific structure of the emphasis map generation unit 6 are described later in the present disclosure.

The B-mode image emphasis adding unit 7 acquires a B-mode image signal from the B-mode image acquisition unit 5 and acquires an emphasis map from the emphasis map generation unit 6. Further, the B-mode image emphasis adding unit 7 adds emphasis to pixel areas of the B-mode image signal. The B-mode image emphasis adding unit 7 adds emphasis to the B-mode image signal, which is the reception signal, such that a pixel area emphasized with a greater emphasis has greater luminance. The B-mode image emphasis adding unit 7 outputs the B-mode image signal with respect to which emphasis adding has been performed to the display control unit 8.

The display control unit 8 causes the display 10 connected thereto to display the emphasis-added B-mode image signal.

The controller 9 is an interface with which the parameters "intensity", "image lag", and "emphasize with color" can be input to the emphasis map generation unit 6. For example, the controller 9 is a pointing device such as a trackball or a mouse.

The display 10 is an image display device connectable to the display control unit 8, and for example, is a liquid crystal display or an organic EL display. Note that the display 10 and the controller 9 may be implemented by using a single device such as a touch panel.

Note that the ultrasound image processing circuit 11 is, for example, implemented by using hardware such as a field programmable gate array (FPGA) or an application-specific integrated circuit (ASIC). Further, the ultrasound transmission/reception unit 2, the transmission/reception control unit 3, the B-mode image generation unit 4, the B-mode image emphasis adding unit 7, and the display control unit 8 are implemented as functional blocks of the ultrasound image processing circuit 11.

<Emphasis Map Generation Unit>

The following describes the structure of the emphasis map generation unit 6.

Figure 2:
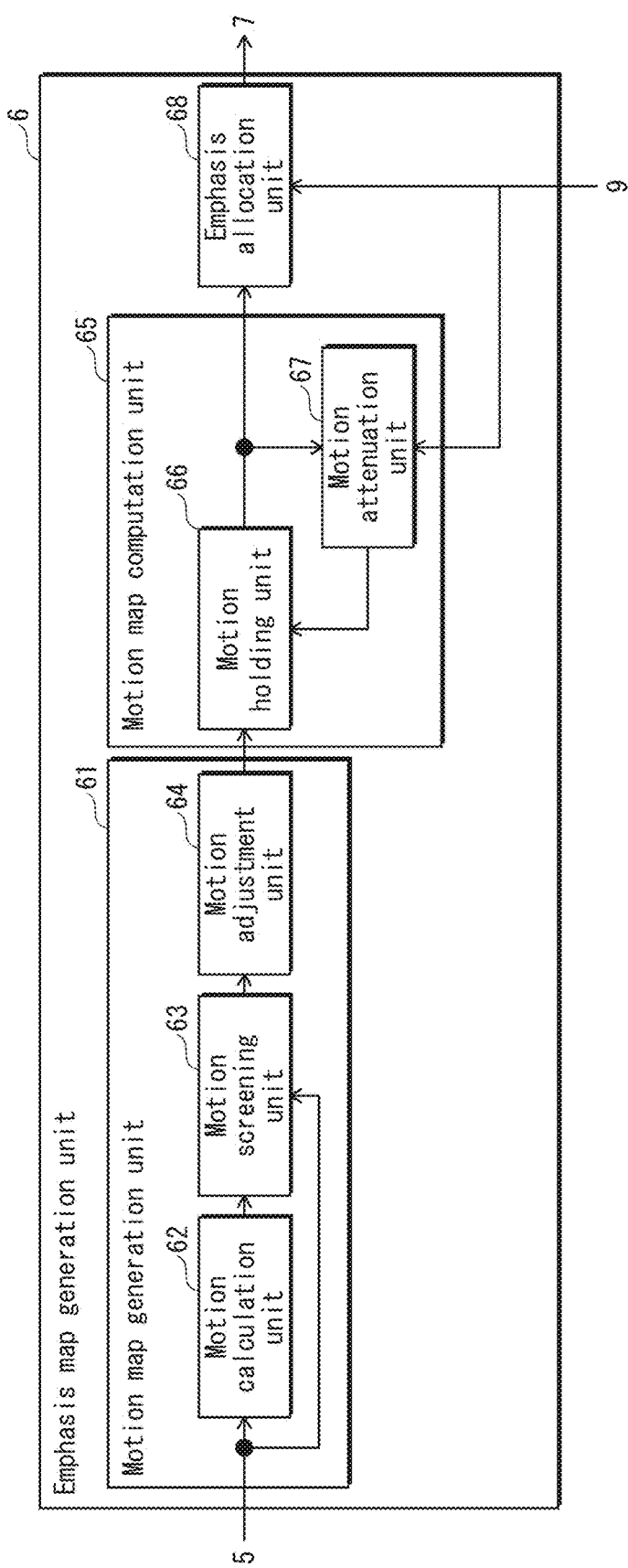
FIG. 2 is a block diagram illustrating an emphasis map generation unit 6 pertaining to embodiment 1.

FIG. 2 is a block diagram illustrating the emphasis map generation unit 6. The emphasis map generation unit 6 includes: a motion map generation unit 61; a motion map computation unit 65; and an emphasis allocation unit 68.

The motion map generation unit 61 generates a motion map based on two B-mode images stored in the B-mode image acquisition unit 5. The motion map is generated by calculating the difference between the two B-mode images, and indicates the motion for each pixel area. In the present disclosure, a motion is a value indicating a signal change corresponding to the movement of a target object between B-mode image signals. More specifically, in the present embodiment, a motion is the difference between the squares of the luminance values of the same pixel area in two B-mode images. Further, in the present disclosure, a pixel area is an area composed of at least one pixel, and is the minimum unit with respect to which processing such as processing of the emphasis map and B-mode image emphasis adding is performed. In the present embodiment in particular, one pixel area corresponds to one pixel. As such, performing processing with respect to pixel areas substantially equals performing processing with respect to pixels.

The motion map generation unit 61 includes a motion calculation unit 62; a motion screening unit 63; and a motion adjustment unit 64.

The motion calculation unit 62, when the B-mode image acquisition unit 5 acquires a B-mode image signal, generates a motion map by using the difference between the B-mode image signal obtained by the B-mode image acquisition unit 5 (i.e., the B-mode image signal of the latest frame) and a B-mode image signal of a previous frame.

The motion screening unit 63 acquires a motion map from the motion calculation unit 62 and acquires a B-mode image signal of the latest frame from the B-mode image acquisition unit 5. Further, the motion screening unit 63 performs weighting with respect to the motion map by using luminance values of the B-mode image signal. In specific, the motion screening unit 63 performs weighting with respect to pixels of the motion map. In specific, the weighting here is performed such that the higher the luminance value of a corresponding pixel of the B-mode image signal, the greater the amount by which the motion of a pixel of the motion map is increased in the weighting. Weighting is performed in such a manner because a puncture needle typically corresponds to pixels (pixel areas) in a B-mode image signal having high luminance values, and by performing weighting in such a manner, pixels areas in the motion map that are likely to correspond to the puncture needle can be provided with relatively great motions.

The motion adjustment unit 64 acquires the motion map with respect to which the motion screening unit 63 has performed weighting, and performs weighting with respect to the motion map based on the total of the motions in the motion map. In specific, the motion adjustment unit 64 calculates a total motion, which is the sum of the motions of every pixel of the motion map. Subsequently, the motion adjustment unit 64, based on a non-increasing function such as that illustrated in FIG. 5A, performs weighting uniformly with respect to every pixel in the motion map by using a weighting coefficient corresponding to the total motion. In specific, the weighting here is performed such that the greater the total motion, the greater the amount by which the motions of the pixels of the motion map are decreased in the weighting. The weighting here is performed in such a manner because when movement of the ultrasound probe 1 occurs, a motion is detected for most pixels, and the total motion of the motion map becomes greater compared to when movement of the ultrasound probe 1 does not occur. By performing weighting in such a manner, a situation is prevented where emphasis is added to the entire B-mode image signal to movement of the ultrasound probe 1.

The motion map computation unit 65 includes a motion holding unit 66 and a motion attenuation unit 67.

The motion holding unit 66, or more specifically, a storage medium included in the motion holding unit 66, holds a motion map (referred to in the following as a second motion map) differing from the motion map generated by the motion map generation unit 61 (referred to in the following as a first motion map). The motion holding unit 66 acquires the first motion map from the motion map generation unit 61, and by using the first motion map and the second motion map, generates a new motion map (referred to as a third motion map in the following). In specific, the motion holding unit 66 compares, pixel-by-pixel, the motion in the first motion map and the motion in the second motion map, and thereby determines the greater one of such motions. Further, by using such motions, the motion holding unit 66 generates the third motion map. The motion holding unit 66 outputs the third motion map to the motion attenuation unit 67 and the emphasis allocation unit 68.

The motion attenuation unit 67 acquires a third motion map from the motion holding unit 66 and attenuates the motions in the third motion map. In specific, the motion attenuation unit 67 causes the motion of each pixel in the third motion to attenuate by multiplying the motion by an attenuation factor that is greater than zero and smaller than one. Here, the smaller the attenuation factor, the greater the attenuation, and the greater the attenuation factor, the smaller the attenuation. The attenuation factor is set according to the image lag time (the amount of time during which image lag persists) input via the controller 9 and the frame rate of the B-mode image signal. In specific, the shorter the image lag time, the smaller the attenuation factor, and the lower the frame rate, the smaller the attenuation factor. For example, when the image lag time is four seconds and the frame rate is 30 frames per second, the attenuation factor is set to 0.989 so that added emphasis decreases by around 50% within two seconds. The motion attenuation unit 67 outputs the third motion map whose motions have been attenuated to the motion holding unit 66. The motion holding unit 66 holds the attenuated third motion map in the storage medium. Thus, the motion holding unit 66 is able to use the attenuated third motion map as a second motion map when generating a third motion map for a subsequent frame.

The emphasis allocation unit 68 acquires a third motion map from the motion map computation unit 65. The emphasis allocation unit 68 converts the motions in the third motion map into emphasis, and thereby creates an emphasis map. An emphasis allocated to a given pixel of the emphasis map is determined according to the motion of the corresponding pixel of the third motion map, and in addition, the "intensity" and "emphasize with color" parameters input via the controller 9.

Further, the motion calculation unit 62, the motion screening unit 63, the motion adjustment unit 64, the motion holding unit 66, the motion attenuation unit 67, and the emphasis allocation unit 68 are implemented as functional blocks of the motion map generation unit 61. Further, note that the motion holding unit 66 has a storage medium that may be implemented, for example, by using a RAM, a flash memory, and/or a hard disk drive.

<Operations>

Figure 11:
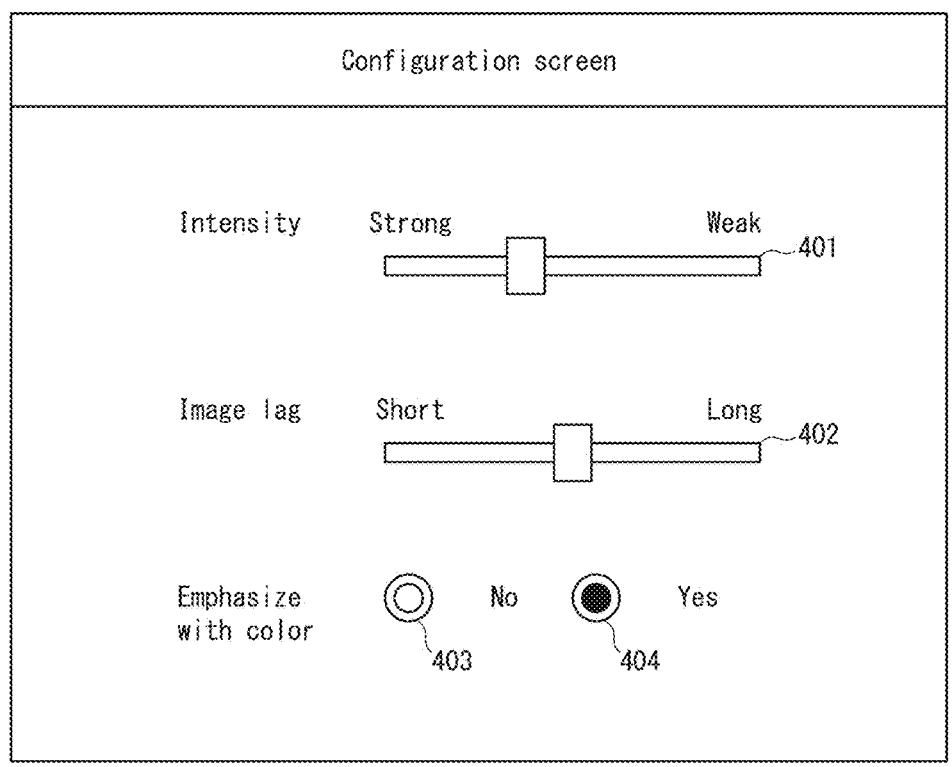
FIG. 11 illustrates one example of a screen for receiving input via a controller 9.

First, the ultrasound diagnostic device 100 receives configuration of "intensity", "image lag", and "emphasize with color". In specific, the ultrasound diagnostic device 100 displays a configuration screen such as that illustrated in FIG. 11 on the display 10, and allows the operator to perform input via the controller 9. In specific, the operator configures "intensity" by using a slider bar 401, configures "image lag" by using a slider bar 402, and configures "emphasize with color" by using option buttons 403, 404. When "intensity" is configured, the intensity of the emphasis added changes. When "image lag" is configured, the time for which added emphasis visually persists changes. When "emphasize with color" is configured, a choice is made of whether or not to add emphasis in color. Note that when the operator does not perform any input with respect to one or more of such parameters, values that are preset to the ultrasound diagnostic device 100 are used.

Figure 3:
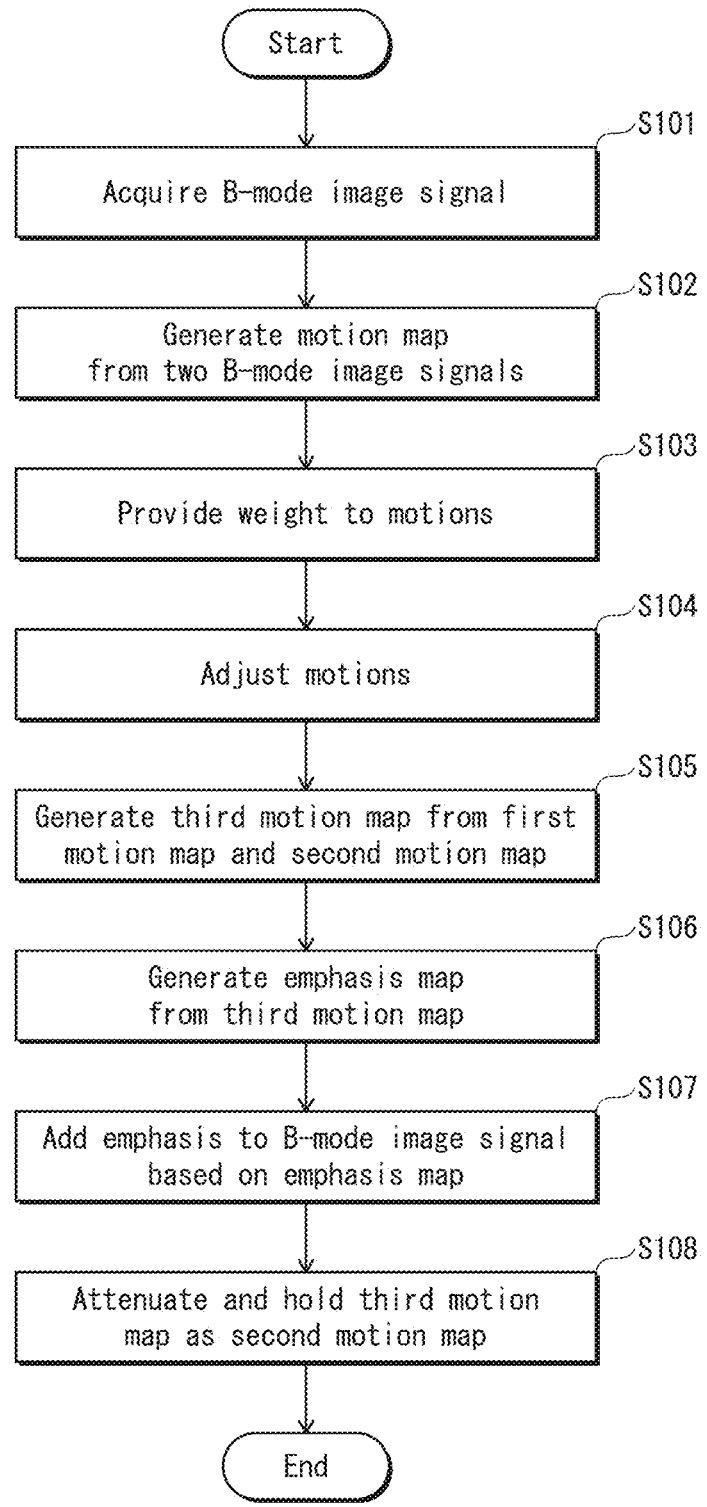
FIG. 3 is a flowchart illustrating operations of the ultrasound diagnostic device 100 pertaining to embodiment 1.

The following describes the operations that the ultrasound diagnostic device 100 performs with respect to each reception signal. FIG. 3 is a flowchart illustrating operations that the ultrasound diagnostic device 100 performs for one reception signal (i.e., one frame).

First, the ultrasound diagnostic device 100 acquires a reception signal (Step S101). In specific, the ultrasound transmission/reception unit 2 performs transmission with the ultrasound probe 1 in contact with the surface of the imaging subject, whereby the ultrasound probe 1 transmits an ultrasound wave with respect to the inside of the imaging subject. Further, the ultrasound transmission/reception unit 2 performs reception based on the reflected ultrasound wave reflected from the imaging subject, which are received via the ultrasound probe 1, whereby an echo signal is generated. Note that the ultrasound transmission/reception unit 2 performs such transmission and reception for a number of times in accordance with the number of transducers provided to the ultrasound probe 1. Thus, a single ultrasound scan is completed, and one frame composed of a plurality of echo signals is formed. Thus, each time an ultrasound scan is performed, one frame echo signal is composed, and the frame echo signal is output to the B-mode image generation unit 4. The B-mode image generation unit 4 receives the frame echo signal as input, and generates a B-mode image signal therefrom. Each time an ultrasound scan is performed, the B-mode image generation unit 4 outputs a B-mode image signal to the B-mode image acquisition unit 5.

Subsequently, the motion calculation unit 62 generates a motion map (Step S102). In specific, the motion calculation unit 62 reads the B-mode image signal acquired by the B-mode image acquisition unit 5, which corresponds to the latest frame, and a B-mode image signal corresponding to the previous frame, and generates a motion map by calculating a motion for each pixel area.

Figure 4C:
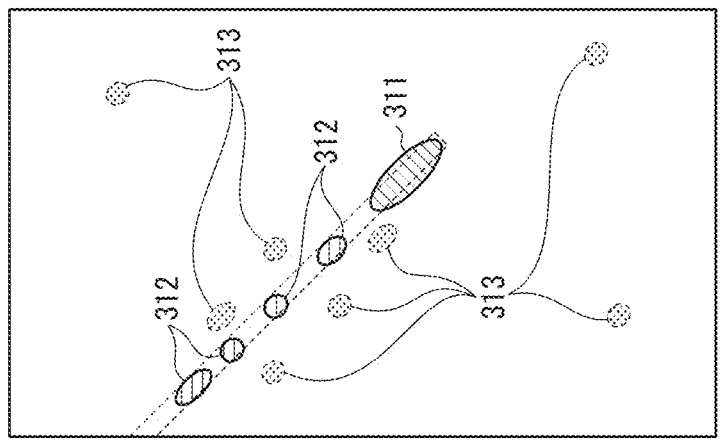
FIG. 4C illustrates a motion map after a motion screening unit 63 performs screening.
Figure 4B:
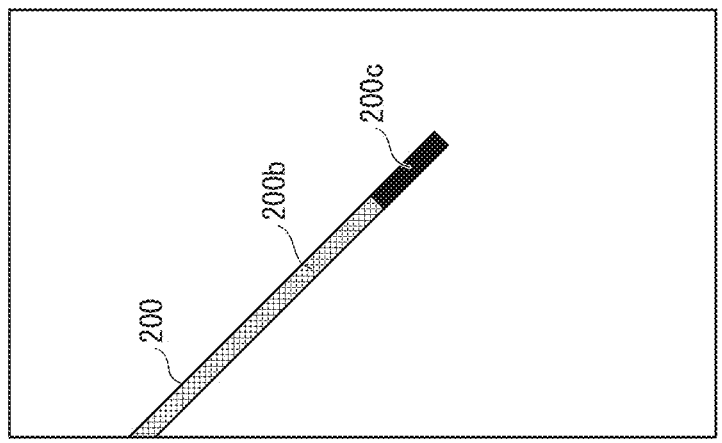
FIG. 4B illustrates a B-mode image held by a B-mode image acquisition unit 5.
Figure 4A:
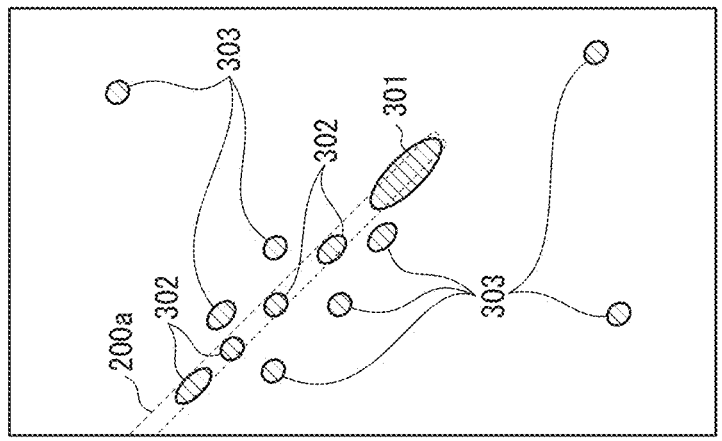
FIG. 4A illustrates a motion map generated by a motion calculation unit 62.

Next, the motion screening unit 63 performs screening of motions (Step S103). In specific, the motion screening unit 63 acquires the motion map from the motion calculation unit 62 and acquires the B-mode image signal corresponding to the latest frame from the B-mode image acquisition unit 5. The motion screening unit 63 performs weighting with respect to the motion map by using the luminance values of the B-mode image signal. FIG. 4A illustrates one example of a motion map, and FIG. 4B illustrates one example of a B-mode image signal. FIG. 4B illustrates a puncture needle 200, which has a tip portion 200c and a tubular potion 200b. In the B-mode image, the tip portion 200c has higher luminance than the tubular potion 200b. Note that in FIG. 4B and in other drawings illustrating B-mode image signals, pixel areas with high luminance values are illustrated in black and pixel areas with low luminance values are illustrated in white, with the exception of FIGS. 9A and 9B. FIG. 4A illustrates a dashed line 200a, which indicates the actual position of the puncture needle. Further, FIG. 4A illustrates areas 302 and 303 where motions exist (motions are not zero). Each area 302 corresponds to a part of the puncture needle, whereas areas 303 do not correspond to parts of the puncture needle. FIG. 4C illustrates the result of the weighting performed with respect to the motion map illustrated in FIG. 4A. As illustrated in FIG. 4C, as a result of the weighting, the motions in area 311 at the tip portion 200c (corresponding to area 301 in FIG. 4A) and areas 312 along the tubular potion 200b (corresponding to areas 302 in FIG. 4A) remain high after the weighting, whereas the motions in areas 313 not corresponding to parts of the puncture needle (corresponding to areas 303 in FIG. 4A) are lower after the weighting compared to before the weighting, due to the low luminance that pixel areas of the B-mode image signal corresponding to such areas have. As a result, motions are screened such that in the weighted B-mode image signal, motions exist only at those pixel areas that are assumed as corresponding to the puncture needle.

Subsequently, the motion adjustment unit 64 performs the adjustment of motions (Step S104). In specific, the motion adjustment unit 64 first calculates a total motion by summing the motions for every pixel in the motion map. Subsequently, the motion adjustment unit 64, based on a non-increasing function such as that illustrated in FIG. 5A, performs weighting with respect to every pixel in the motion map by using a weighting coefficient corresponding to the total motion. Note that when there is no change in the position or orientation of the ultrasound probe 1 between the B-mode image signal for the latest frame and the B-mode image signal for the previous frame, in the motion map with respect to the motion screening unit 63 has performed screening, only pixel areas corresponding to and around the puncture needle would have relatively great motions, as illustrated in FIG. 6A. In contrast, when there is a change in the position and/or orientation of the ultrasound probe 1 between the B-mode image signal for the latest frame and the B-mode image signal for the previous frame, in the motion map with respect to the motion screening unit 63 has performed screening, motions would exists almost at an entirety of pixel areas 321 other than pixels areas corresponding to and around the puncture needle, as illustrated in FIG. 6B. In other words, motions are detected at almost all pixel areas of the motion map. Seen in another way, the total motion calculated by the motion adjustment unit 64 indicates the amount of movement of the ultrasound probe 1. Thus, by performing weighting such that motions in the motion map are reduced in accordance with the total motion, a situation is prevented where emphasis is added to an entire B-mode image signal due to movement of the ultrasound probe 1.

Figure 7A:
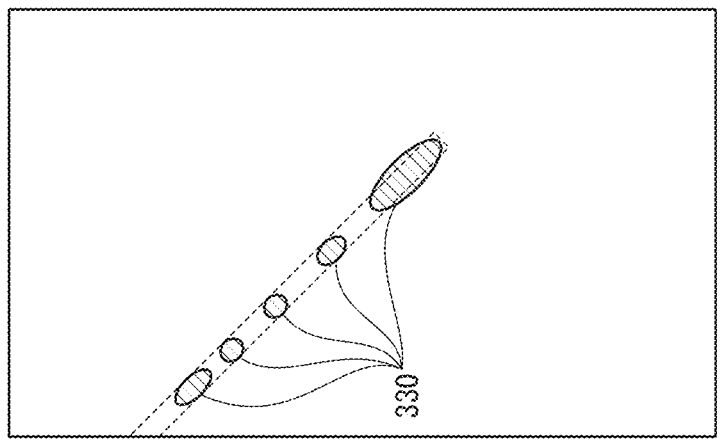
FIG. 7A illustrates one example of a first motion map.
Figure 7B:
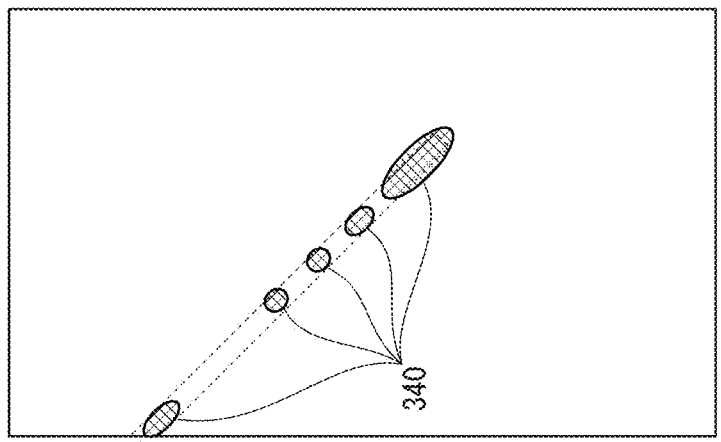
FIG. 7B illustrates one example of a second motion map.
Figure 7C:
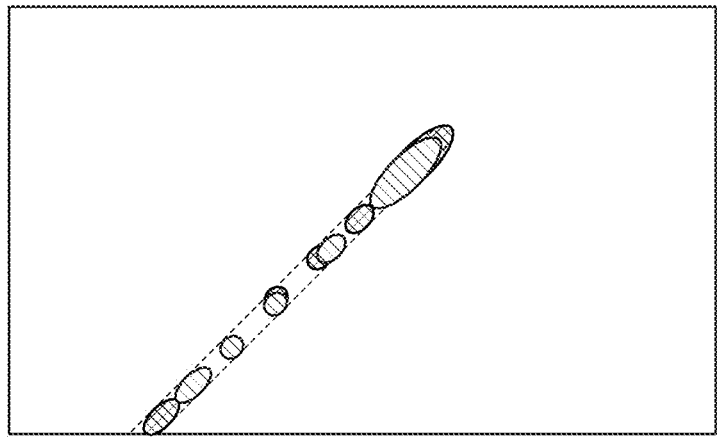
FIG. 7C illustrates one example of a third motion map.
Figure 9A:
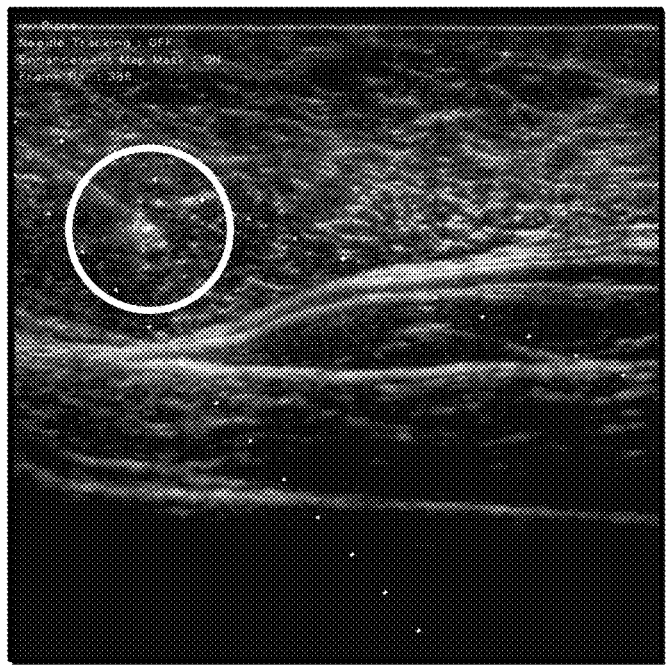
FIG. 9A illustrates a B-mode image after emphasis is added through conventional emphasis adding.
Figure 9B:
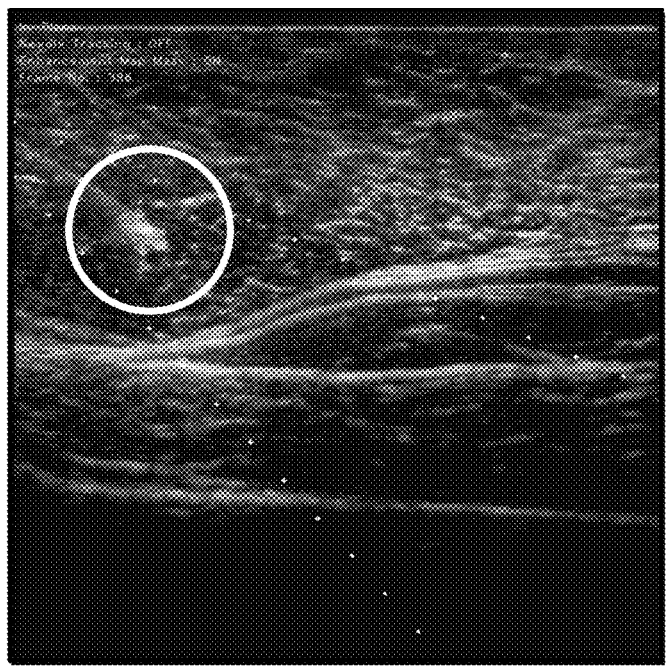
FIG. 9B illustrates a B-mode image after emphasis is added through emphasis adding pertaining to embodiment 1.

Subsequently, the motion holding unit 66 generates a third motion map (Step S105). In specific, the motion holding unit 66 compares the motion at a given mapping position (i.e., a pixel area indicated by a given set of coordinates) in the first motion map and the motion at the corresponding mapping position (i.e., a pixel area indicated by the same set of coordinates) in the second motion map, and thereby determines the greater one of such motions as the motion of a pixel area indicated by the same set of coordinates in the third motion map. The motion holding unit 66 performs such processing with respect to all pixel areas, and thereby generates the third motion map. FIGS. 7A, 7B, and 7C illustrate the first, second, and third motion maps, respectively. In each of FIGS. 7A through 7C, the area surrounded by the dashed line indicates the actual position of the puncture needle. Here, say the areas 330 in the first motion map have greater motions than the areas 340 in the second motion map. In such a case, motions in the third motion map (FIG. 7C) are calculated as follows. Motions in the third motion map at pixel areas corresponding to the area 330 in the first motion map are calculated to be the respective motions at the areas 330. Further, motions in the third motion map at pixel areas that do not correspond to the area 330 in the first motion map but correspond to the area 340 in the second motion map are calculated to be the respective motions at the areas 340. Finally, motions in the third motion map that correspond neither to the area 330 in the first motion map nor the area 340 in the second motion map are calculated to have the value zero. When motions are detected by merely calculating differences between two B-mode images, the detected motions tend to be sparsely distributed as illustrated in FIG. 9A. In contrast, according to the present embodiment, the detected motions can be accumulated over time, and thus can be visualized in a densely distributed manner as illustrated in FIG. 9B. Further, since motions can be accumulated, motions calculated in the past can be visualized in the form of image lags.

Next, the emphasis allocation unit 68 generates an emphasis map based on the third motion map (Step S106). In specific, the emphasis amount allocation unit 68 generates the emphasis map by converting motions of pixels of the third motion map into emphasis based on the parameters "intensity" and "emphasize with color". The conversion of motions in the third motion map into emphasis is performed as follows. When the "emphasize with color" parameter indicates that a configuration is made to add emphasis with color, each motion is converted into a value by using a non-decreasing function, and the values so yielded are converted into emphasis indicating color by using the value of the "intensity" parameter. Meanwhile, when the "emphasize with color" parameter indicates that a configuration is made not to add emphasis with color, each motion is converted into a value by using a non-decreasing function, and the values so yielded are converted into emphasis influencing luminance by using the value of the "intensity" parameter.

Figure 8C:
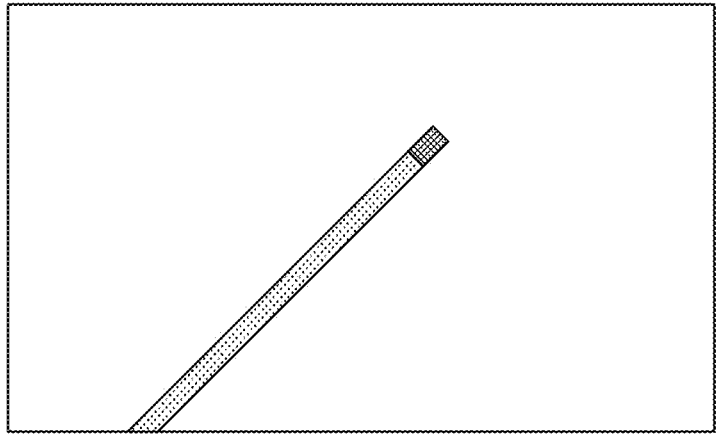
FIG. 8C illustrates a B-mode image after a B-mode image emphasis adding unit 7 performs emphasis adding.
Figure 8B:
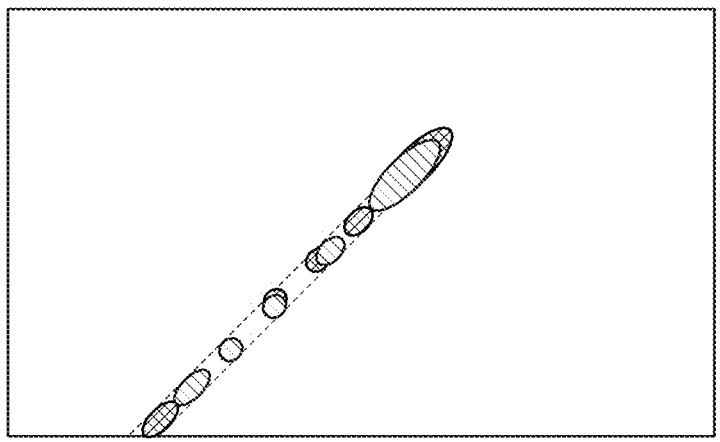
FIG. 8B illustrates an emphasis map generated by an emphasis map allocation unit 68.
Figure 8A:
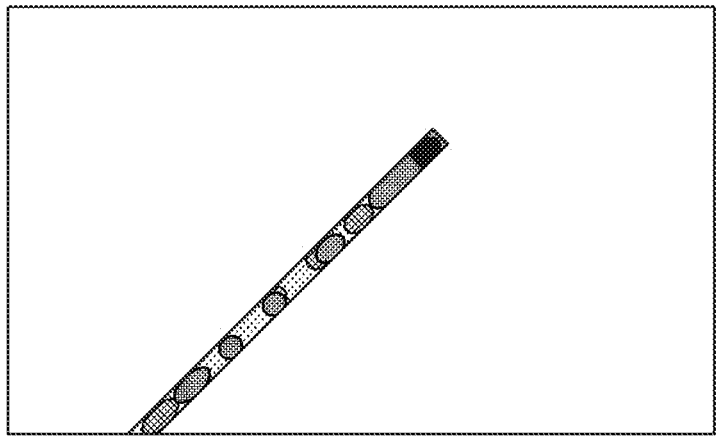
FIG. 8A illustrates a B-mode image held by the B-mode image acquisition unit 5.

Then, the B-mode image emphasis adding unit 7 performs emphasis adding according to the emphasis map (Step S107). FIG. 8C illustrates a B-mode image that is yielded by adding emphasis to the B-mode image signal illustrated in FIG. 8A by using the emphasis map illustrated in FIG. 8B. The B-mode image so generated is displayed on the display 10 by the display control unit 8.

Finally, the motion attenuation unit 67 performs attenuation of the third motion map (Step S108). In specific, the motion attenuation unit 67 attenuates motions of pixel areas of the third motion map based on an attenuation factor. As already described above, the attenuation factor is set according to the "image lag" parameter and frame rate. The attenuated third motion map is stored to the storage medium included in the motion holding unit 66, and is used as the second motion map in the processing performed with respect to a subsequent frame. FIG. 10 is a schematic diagram illustrating the relationship between the first, second, and third motion maps. A third motion map 3a that is created based on a first motion map 1a and a second motion map 2a is stored to the storage medium included in the motion holding unit 66 after motions therein are attenuated by the motion attenuation unit 67. The attenuated third motion map 3a stored in the storage medium is used as a second motion map 2b in processing performed with respect to a subsequent frame in combination with a first motion map 1b, for generating a third motion map 3b. The third motion map 3b is also stored to the storage medium after motions therein are attenuated by the motion attenuation unit 67. The attenuated third motion map 3b is used as a second motion map 2c in processing performed with respect to a subsequent frame in combination with a first motion map 1c, for generating a third motion map 3c. Here, note that the third motion map 3a becomes the second motion map 2b through attenuation of motions, and similarly, the third motion map 3b becomes the second motion map 2c through attenuation of motions. Due to this, the influence that the motions in the first motion map 1a has on the third motion map decreases, each time the third motion map is updated. That is, the influence that the motions in the first motion map 1a is greatest in the creation of the third motion map 3a, becomes smaller in the creation of the third motion map 3b, and becomes even smaller in the creation of the third motion map 3c. It is due to the attenuation of motions being performed as described above that emphasis added continues to be displayed during the time set to "image lag".

<Summary>

The structure described above provides the third motion map, in which signal changes corresponding to the movement of a puncture needle are accumulated. Thus, the present embodiment achieves adding emphasis to signal changes corresponding to the movement of a puncture needle at higher spatial density than conventionally possible, thereby improving the visual perceptibility of puncture needles. Meanwhile, each time the processing target frame changes, motions in the second motion map that reflect motions in past first motion maps are attenuated. Thus, while added emphasis continues to be displayed for a certain period of time as an image lag and thus does not disappear immediately, added emphasis does not persist to be displayed over an undesirably long period of time.

In addition, when movement of the ultrasound probe occurs, adjustment of motions is performed so that adding of emphasis is suppressed. Due to this, the situation is prevented where emphasis is added over the entire screen due to movement of the ultrasound probe. Further, even when movement of the ultrasound probe occurs, there is no need to for the operator to perform operations for suspending the adding of emphasis.

<Modification of Embodiment 1>
<Structure>

Figure 12:
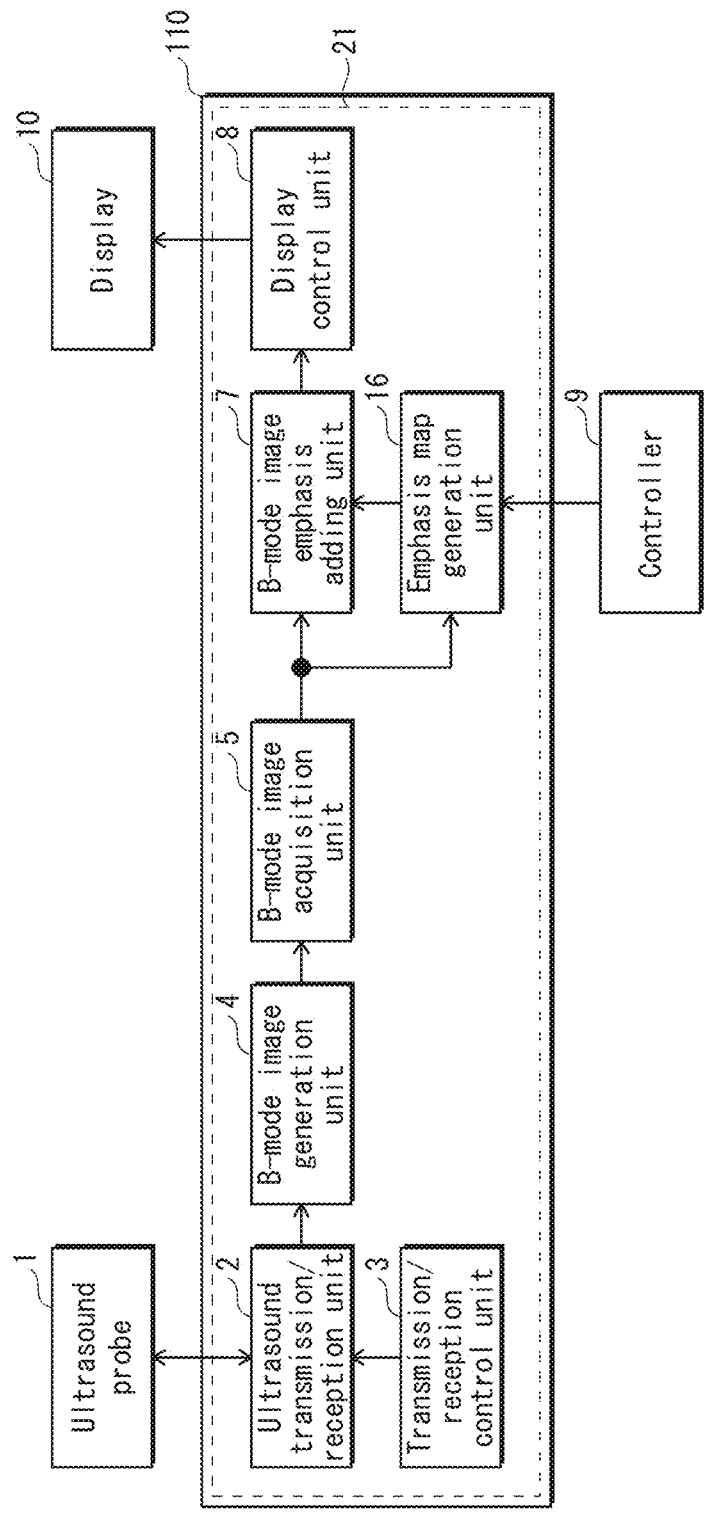
FIG. 12 is a block diagram illustrating an ultrasound diagnostic device 110 pertaining to a modification of embodiment 1.

FIG. 12 is a block diagram illustrating a ultrasound diagnostic device 110 pertaining to a modification of embodiment 1. Note that in FIG. 11, components already illustrated in FIG. 1 are indicated by using the same reference signs. Further, such components are not described in detail in the following.

The ultrasound diagnostic device 110 has a structure similar to that of the ultrasound diagnostic device 100, differing from the ultrasound diagnostic device 100 only for including an ultrasound image processing circuit 21 including an emphasis map generation unit 16, instead of the ultrasound image processing circuit 11 including the emphasis map generation unit 6.

Figure 13:
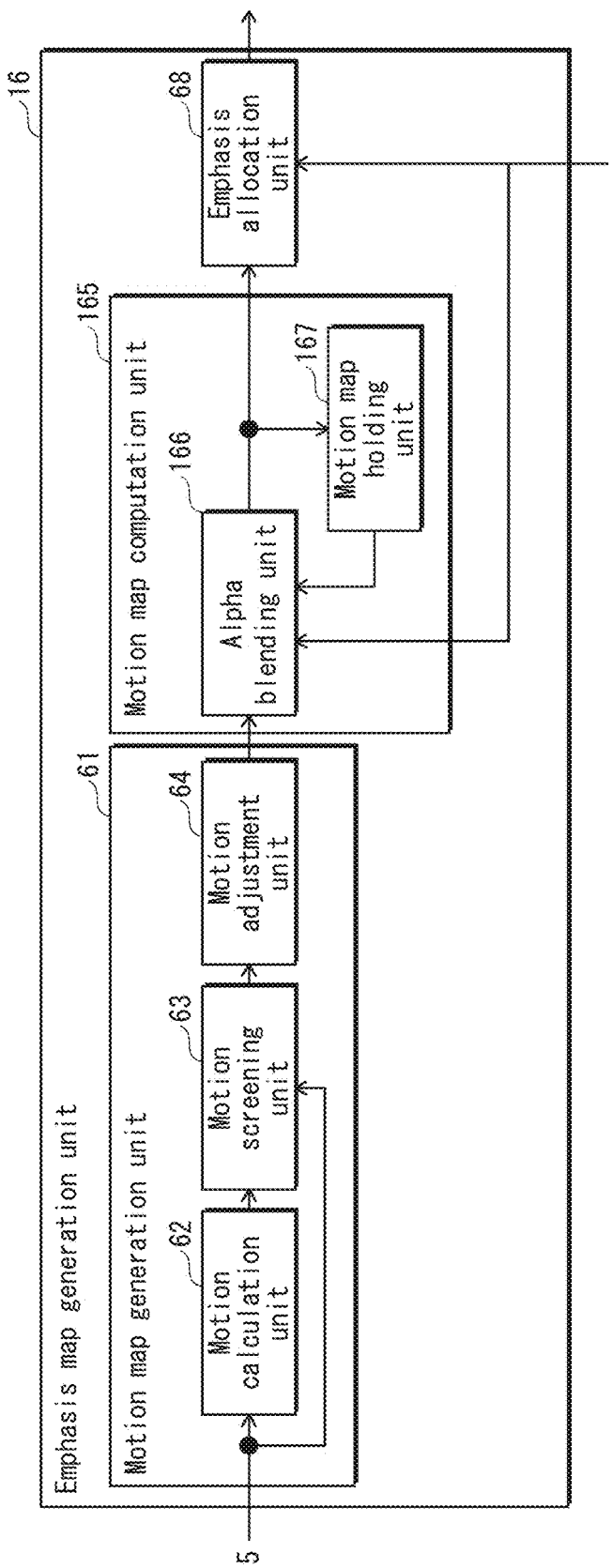
FIG. 13 is a block diagram illustrating an emphasis map generation unit 16 pertaining to the modification of embodiment 1.

FIG. 13 is a block diagram illustrating the emphasis map generation unit 16. Note that in FIG. 13, components already illustrated in FIG. 2 are indicated by using the same reference signs. Further, such components are not described in detail in the following.

The emphasis map generation unit 16 has a structure similar to that of the emphasis map generation unit 6, differing from the emphasis map generation unit 6 only in that the motion map computation unit 65 is replaced with a motion map computation unit 165. The motion map computation unit 165 includes an alpha blending unit 166 and a motion map holding unit 167.

The alpha blending unit 166 generates a third motion map by using a first motion map generated by the motion map generation unit 61 and a motion map stored in the motion map holding unit 167 (referred to in the following as a fourth motion map). In specific, the alpha blending unit 166 regards the motions in each of the first motion map and the fourth motion map as pixel values, and performs alpha blending of the first motion map and the fourth motion map. Thus, the first motion map and the fourth motion map are composited into a single motion map (third motion map). Alpha-blending refers to pixel-by-pixel processing where a pixel value (motion) of a given pixel in the first motion map and a pixel value (motion) of a corresponding pixel in the fourth motion map are linearly combined at a ratio of $(1-\alpha):\alpha$ (where $\alpha$ represents a predetermined alpha value satisfying $0<\alpha<1$), and the value obtained through the linear combination is set as a pixel value (motion) of a corresponding pixel in the third motion map. That is, given $V_1$ denoting the motion of a pixel at a given set of coordinates in the first motion map, $V_4$ denoting the motion of a pixel at the same set of coordinates in the fourth motion map, and $V_3$ denoting the motion of a pixel at the same set of coordinates in the third motion map, $V_1$, $V_4$, and $V_3$ satisfy: $V_3=(1-\alpha)\times V_1+\alpha\times V_4$. The value α changes depending upon the image lag time set via the controller 9 and the frame rate of the B-mode image signal. Similar to the above-described attenuation factor, the shorter the image lag time, the smaller the value α, and the lower the frame rate, the smaller the value α. For example, when the image lag time is one second and the frame rate is 20 frames per second, the value α is set to 0.93 so that added emphasis decreases by around 50% in 0.5 seconds.

The motion map holding unit 167 is a storage medium storing the fourth motion map. In specific, the motion map holding unit 167, when the alpha blending unit 166 generates a third motion map, stores the third motion map as-is as a fourth motion map, and outputs the fourth motion map to the alpha blending unit 166 in the processing performed with respect to a subsequent frame.

<Operations>

First, the ultrasound diagnostic device 110 receives configuration of "intensity", "image lag", and "emphasize with color". Since the processing here is similar to that in embodiment 1, detailed description thereof is not provided in the following.

Figure 14:
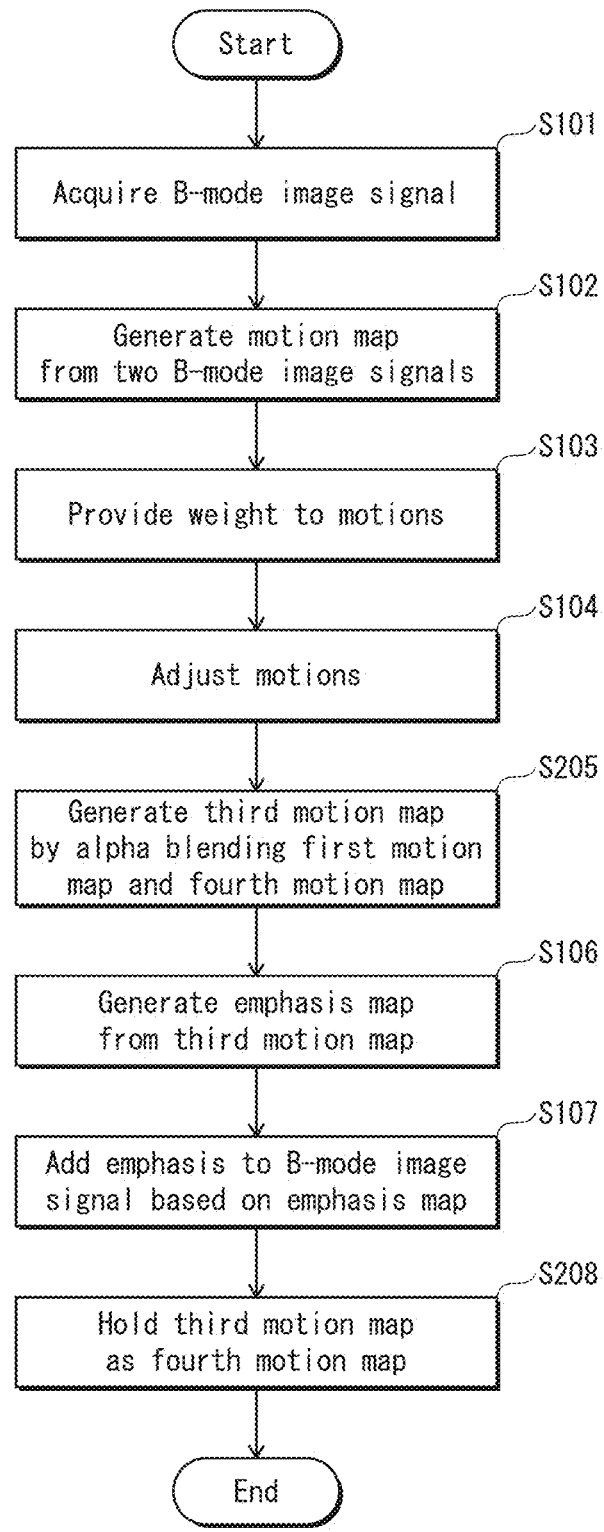
FIG. 14 is a flowchart illustrating operations of the ultrasound diagnostic device 110 pertaining to the modification of embodiment 1.

The following describes the operations that the ultrasound diagnostic device 110 performs with respect to each reception signal. FIG. 14 is a flowchart illustrating operations that the ultrasound diagnostic device 110 performs for one reception signal (one frame).

Note that the same reference signs in FIGS. 3 and 14 indicate the same processing, and thus, detailed description thereof is not provided in the following.

First, the ultrasound diagnostic device 110 acquires a reception signal (Step S101).

Subsequently, the motion calculation unit 62 generates a motion map (Step S102).

Next, the motion screening unit 63 performs screening of motions (Step S103).

Then, the motion adjustment unit 64 performs adjustment of motions (Step S104).

Following this, the alpha blending unit 166 generates a third motion map (Step S205). In specific, the alpha blending unit 166 performs pixel-by-pixel processing where a motion of a given pixel in a first motion map generated by the motion map generation unit 61, and a motion of a corresponding pixel in the fourth motion map being held by the motion map holding unit 167, are linearly combined at a ratio of $(1-\alpha):\alpha$, and the value obtained through the linear combination is set as a motion of a corresponding pixel in the third motion map. Thus, emphasis is added to areas of a processing-target B-mode image where signal changes corresponding to movement are detected continuously over time, while the adding of emphasis to areas where signal changes corresponding to movement are sparsely detected over time is suppressed.

Next, the emphasis allocation unit 68 generates an emphasis map based on the third motion map (Step S106).

Then, the B-mode image emphasis adding unit 7 performs emphasis adding according to the emphasis map (Step S107).

Finally, the motion map holding unit 167 stores the third motion map as a fourth motion map (Step S208).

<Summary>

In this modification, a fourth motion map for the latest frame corresponds to a third motion map for a previous frame. Thus, the fourth motion map is similar to the second motion map, differing from the second motion map only in that the fourth motion map is yielded without attenuating the motions in the third motion map with the motion attenuation unit 67. The attenuation by the motion attenuation unit 67 is unnecessary since the alpha value used by the alpha blending unit 166 has the same effects as the attenuation factor used by the motion attenuation unit 67. More specifically, in embodiment 1, the calculation of motions in a third motion map for a latest frame is influenced by motions in a second motion map for the latest frame (i.e., yielded by multiplying motions in a third motion map for a previous frame with the attenuation factor). Meanwhile, in the present modification, the calculation of motions in a third motion map for a latest frame is performed by multiplying motions in a fourth motion map for the latest frame (i.e., corresponding to a third motion map for a previous frame) with the alpha value. The use of the alpha value brings about the same effects as the use of the attenuation factor, because the influence that the third motion map for the previous frame (i.e., the fourth motion map for the latest frame) has on the creation of the third motion map for the latest frame is attenuated by the alpha value.

Thus, the generation of the third motion map by the alpha blending unit 166 in the present embodiment corresponds to the combination, in embodiment 1, of the attenuation of motions by the motion attenuation unit 67 and the generation of the third motion map by the motion holding unit 66.

<Embodiment 2>
<Structure>

Figure 15:
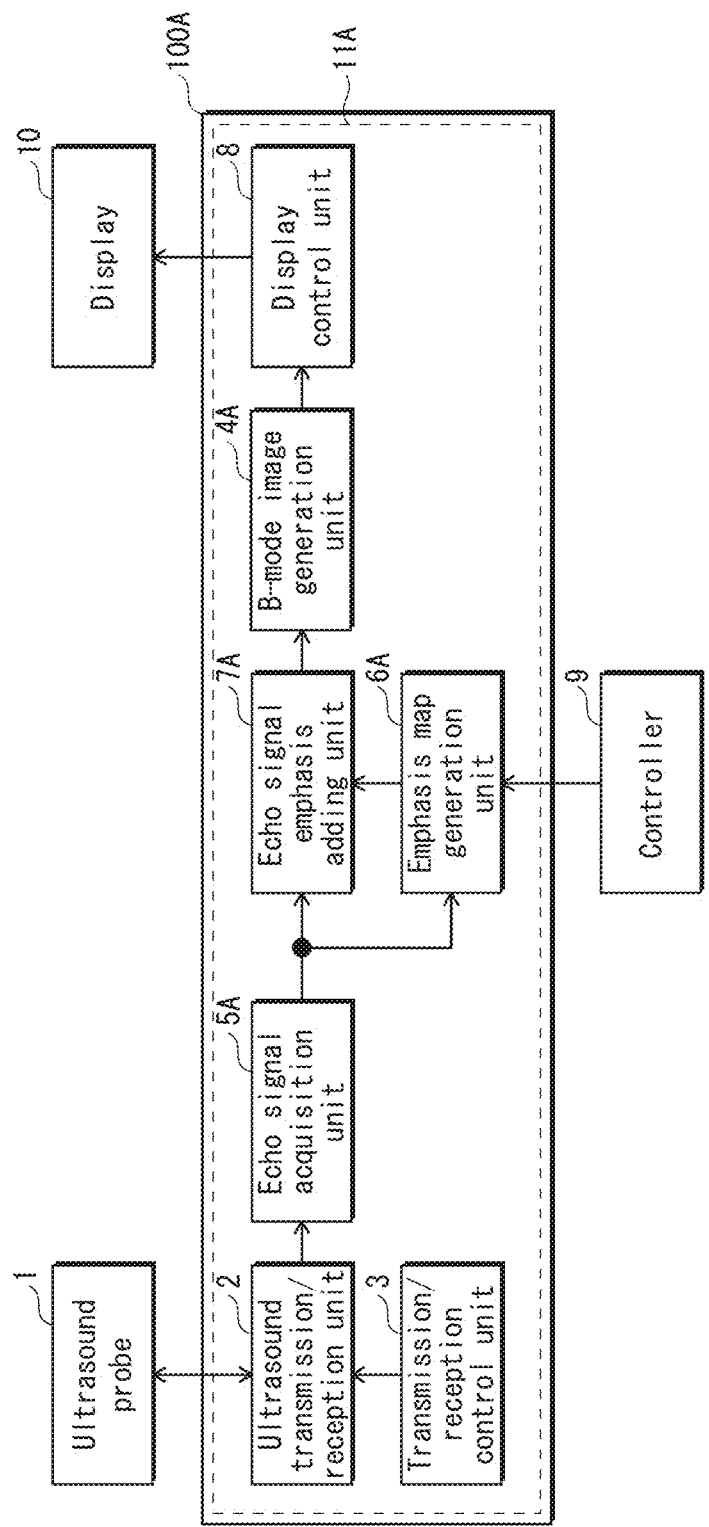
FIG. 15 is a block diagram illustrating an ultrasound diagnostic device 100A pertaining to embodiment 2.

FIG. 15 is a block diagram illustrating a ultrasound diagnostic device 100A pertaining to embodiment 2. Note that in FIG. 15, components already illustrated in FIG. 1 are indicated by using the same reference signs. Further, such components are not described in detail in the following.

The ultrasound diagnostic device 100A is similar to the ultrasound diagnostic device 100, differing from the ultrasound diagnostic device 100 only in that the ultrasound diagnostic device 100A includes an ultrasound image processing circuit 11A in place of the ultrasound image processing circuit 11. The ultrasound image processing circuit 11A is characterized in that an emphasis map is generated with respect to a frame echo signal and emphasis is added to the frame echo signal by using the emphasis map, before the frame echo signal is converted into a B-mode image.

The ultrasound image processing circuit 11A includes an echo signal acquisition unit 5A. The echo signal acquisition unit is a buffer that stores a frame echo signal. As already described above, one frame echo signal is generated for each ultrasound scan performed.

The ultrasound image processing circuit 11A includes an emphasis map generation unit 6A and an echo signal emphasis adding unit 7A. The emphasis map generation unit 6A receives, as input, frame echo signals stored in the echo signal acquisition unit 5A and the parameters "intensity", "image lag", and "emphasize with color" input via the controller 9. The emphasis map generation unit 6A generates an emphasis map, and outputs the emphasis map to the echo signal emphasis adding unit 7A. The emphasis map is a map that causes emphasis to be added to motions corresponding to puncture needle insertion. The operations of the emphasis map generation unit 6A are similar to those of the emphasis map generation unit 6, differing from the operations of the emphasis map generation unit 6 only in that the emphasis map generation unit 6A generates an emphasis map based on frame echo signals and not B-mode image signals.

The echo signal emphasis adding unit 7A acquires a frame echo signal stored in the echo signal acquisition unit 5A and acquires the emphasis map from the emphasis map generation unit 6A. Further, the echo signal emphasis adding unit 7A adds emphasis to pixel areas of the frame echo signal. The operations of the echo signal emphasis adding unit 7A are similar to those of the B-mode image emphasis adding unit 7, differing from the operations of the B-mode image emphasis adding unit 7 only in that the echo signal emphasis adding unit 7A adds emphasis to a frame echo signal and not a B-mode image signal.

The ultrasound diagnostic device 100A includes a B-mode image generation unit 4A. The B-mode image generation unit 4A converts each one of the echo signals with respect to which the echo signal emphasis adding unit 7A has added emphasis into a luminance signal having a luminance value corresponding to the intensity of the emphasis-added echo signal. Further, the B-mode image generation unit 4A performs coordinate conversion on the luminance signals to obtain a signal based on an orthogonal coordinate system. Thus, the B-mode image generation unit 4A generates a B-mode image signal. The B-mode image generation unit 4A performs operations similar to those of the B-mode image generation unit 4, differing from the operations of the B-mode image generation unit 4 only in that the B-mode image generation unit 4A converts, into a B-mode image, the emphasis-added echo signals obtained by the echo signal emphasis adding unit 7A performing emphasis adding, and not the echo signals generated by the ultrasound transmission/reception unit 2.

<Operations>

First, the ultrasound diagnostic device 100A receives configuration of "intensity", "image lag", and "emphasize with color". Since the operations here are similar to those in embodiment 1, detailed description thereof is not provided in the following.

Figure 16:
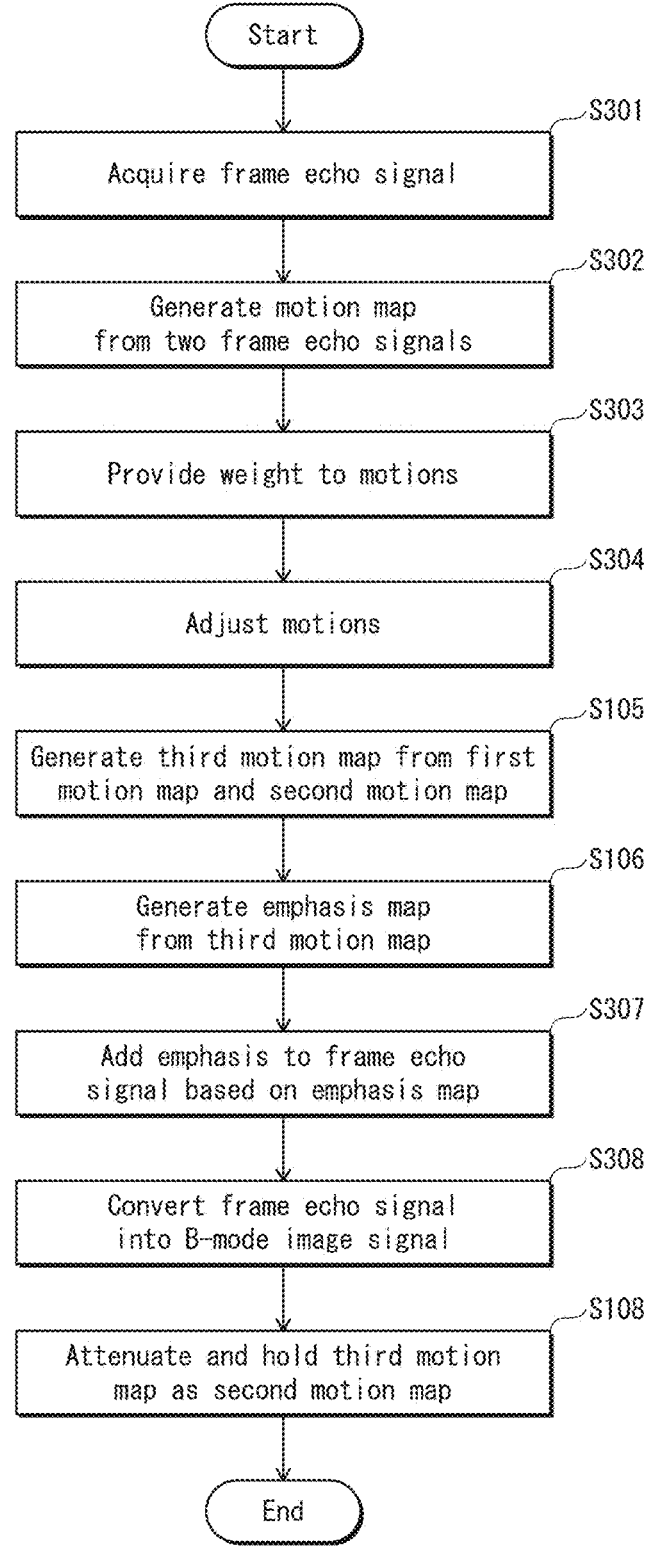
FIG. 16 is a flowchart illustrating operations of the ultrasound diagnostic device 100A pertaining to embodiment 2.

The following describes the operations that the ultrasound diagnostic device 100A performs with respect to each reception signal. FIG. 16 is a flowchart illustrating operations that the ultrasound diagnostic device 100A performs for one reception signal (i.e., one frame). Note that the same reference signs in FIGS. 3 and 16 indicate the same processing, and thus, detailed description thereof is not provided in the following.

First, the ultrasound diagnostic device 100A acquires a reception signal (Step S301). In specific, the ultrasound transmission/reception unit 2 performs transmission with the ultrasound probe 1 in contact with the surface of the imaging subject, whereby the ultrasound probe 1 transmits an ultrasound wave with respect to the inside of the imaging subject. Further, the ultrasound transmission/reception unit 2 performs reception based on the reflected ultrasound wave reflected from the imaging subject, which is received via the ultrasound probe 1, whereby an echo signal is generated. Note that the ultrasound transmission/reception unit 2 performs such transmission and reception for a number of times in accordance with the number of transducers provided to the ultrasound probe 1. Thus, a single ultrasound scan is completed, and one frame composed of a plurality of echo signals is formed. Thus, each time an ultrasound scan is performed, one frame echo signal is formed, and the frame echo signal is output to the echo signal acquisition unit 5A.

Subsequently, the emphasis map generation unit 6A generates a motion map (Step S302). In specific, the emphasis map generation unit 6A generates a motion map by reading the frame echo signal acquired by the echo signal acquisition unit 5A and a previous frame echo signal. The processing in Step S302 differs from the processing in Step S102 only in that frame echo signals are used in place of B-mode image signals. Thus, detailed description thereof is not provided in the following.

Next, the emphasis map generation unit 6A performs screening of motions (Step S303). The processing in Step S303 differs from the processing in Step S103 only in that a motion map based on frame echo signals are used in place of a motion map based on B-mode image signals, and intensity values of a frame echo signal is used in place of luminance values in a B-mode image signal. Thus, detailed description thereof is not provided in the following.

Subsequently, the emphasis map generation unit 6A performs the adjustment of motions (Step S304). The processing in Step S304 differs from the processing in Step S104 only in that a motion map based on frame echo signals are used in place of a motion map based on B-mode image signals. Thus, detailed description thereof is not provided in the following.

Subsequently, the emphasis map generation unit 6A generates a third motion map (Step S105).

Next, the emphasis map generation unit 6A generates an emphasis map by using the third motion map (Step S106).

Then, the echo signal emphasis adding unit 7A performs emphasis adding according to the emphasis map (Step S307). The processing in Step S307 differs from the processing in Step S107 only in that emphasis is added to a frame echo signal and not a B-mode image signal. Thus, detailed description thereof is not provided in the following.

Subsequently, the B-mode image generation unit 4A converts the frame echo signal into a B-mode image signal (Step S308). In specific, the B-mode image generation unit 4A converts each of the echo signals in the frame echo signal with respect to which the echo signal emphasis adding unit 7A has added emphasis into a luminance signal having an intensity value corresponding to the intensity of the emphasis-added echo signal. Further, the B-mode image generation unit 4A performs coordinate conversion on the luminance signals to obtain a signal based on an orthogonal coordinate system. Thus, the B-mode image generation unit 4A generates a B-mode image signal.

Finally, the emphasis map generation unit 6A performs attenuation with respect to the third motion map (Step S108).

<Summary>

In embodiment 2, emphasis is added to echo signals, which are later converted into a B-mode image signal. This enables adding emphasis to a puncture needle even when, for example, the B-mode image generation unit 4A and the display control unit 8 are external units not included in the ultrasound diagnostic device 100A.

<Other Modifications pertaining to Embodiments and Modification>

Figure 17:
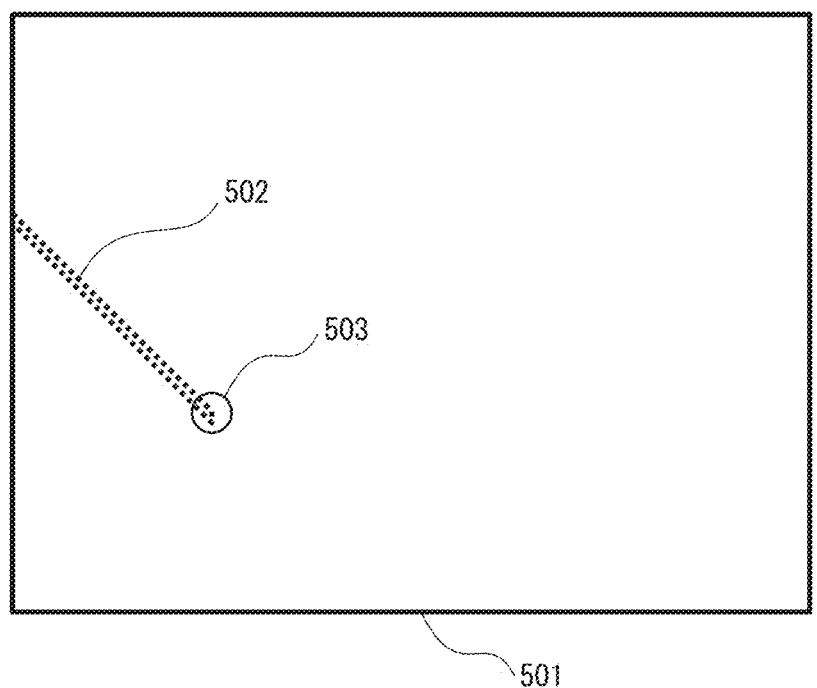
FIG. 17 illustrates one example of B-mode image emphasis adding pertaining to a modification.

(1) In embodiment 1, modification of embodiment 1, and embodiment 2, the emphasis allocation unit 68 converts motions of pixels of the third motion map into emphasis by using a non-decreasing function and the value of the "intensity parameter", such that when the "emphasize with color" parameter indicates that a configuration is made to add emphasis with color, emphasis indicating color is yielded, and when the "emphasize with color" parameter indicates that a configuration is made not to add emphasis with color, emphasis influencing luminance is yielded. However, the emphasis allocation unit 68 need not perform the allocation of emphasis to pixels in such a manner. For example, a modification may be made such that the emphasis allocation unit 68 allocates emphasis indicating color or emphasis influencing luminance values to only pixel areas having motions equal to or greater than a predetermined threshold value. Alternatively, a modification may be made such that when the "emphasize with color" parameter indicates that a configuration is made to add emphasis with color, the emphasis allocation unit 68 allocates to each pixel area both an emphasis indicating color and an emphasis influencing luminance. Alternatively, a modification may be made such that the emphasis allocation unit 68 allocates, to pixel areas having motions equal to or greater than a predetermined threshold value, emphasis indicating that icons are to be overlaid onto such pixel areas. FIG. 17 illustrates an example where a circular icon 503 has been overlaid onto a tip of a puncture needle 502, which corresponds to a pixel area having a motion greater than or equal to a predetermined threshold value. Alternatively, a modification may be made such that the emphasis allocation unit 68 allocates, to a pixel area having the greatest motion, an emphasis indicating that an icon is to be overlaid onto such pixel areas. Alternatively, a modification may be made such that the emphasis allocation unit 68 allocates, when taking a given pixel area for example, a combination of an emphasis indicating that an icon is to be overlaid to the pixel area, and one of an emphasis indicating color tone and an emphasis influencing the luminance value of the pixel area.

Figure 5A:
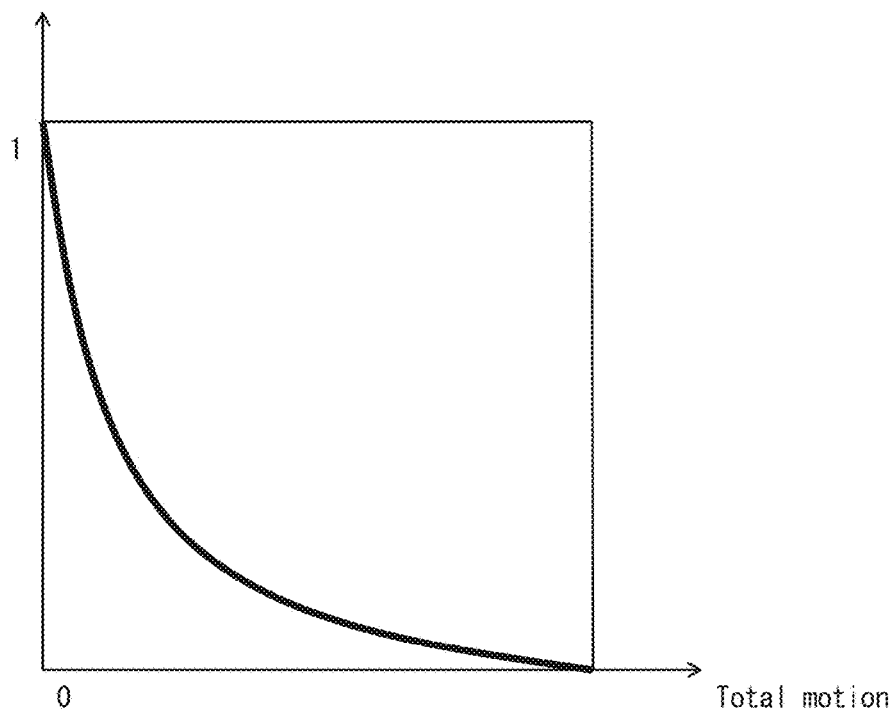
FIG. 5A illustrates a weighting coefficient used by a motion adjustment unit 64 in embodiment 1.
Figure 5B:
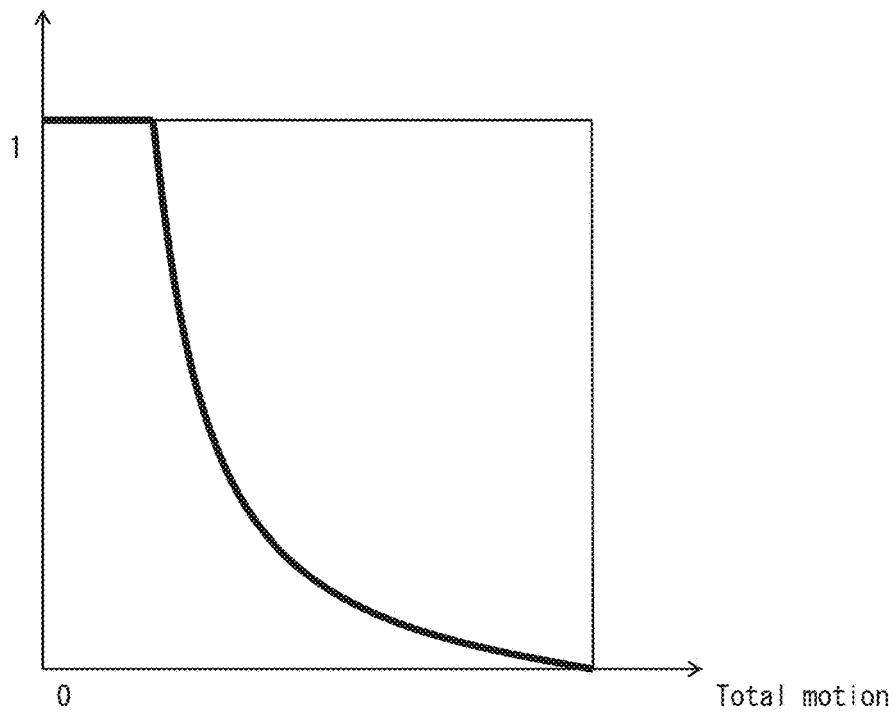
FIG. 5B illustrates a weighting coefficient used by the motion adjustment unit 64 in a modification.
Figure 6A:
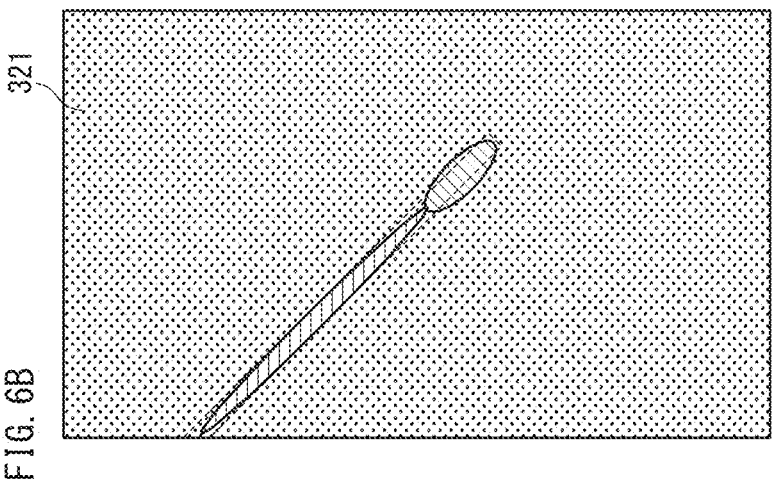
FIG. 6A illustrates one example of a motion map when an ultrasound probe 1 does not move.
Figure 6B:
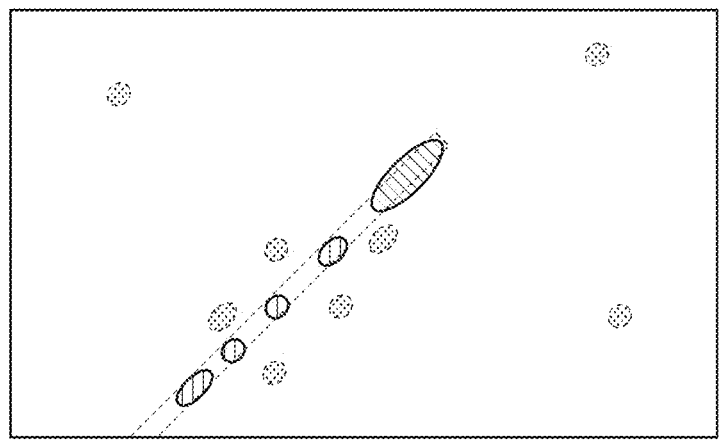
FIG. 6B illustrates one example of a motion map when the ultrasound probe 1 moves.

(2) In embodiment 1, modification of embodiment 1, and embodiment 2, the motion adjustment unit 64 adjusts motions in a motion map based on a total of the motions in the motion map by using the non-increasing function illustrated in FIG. 5A. However, the motion adjustment unit 64 need not adjust motions in a motion map in such a manner. For example, a modification may be made such that the motion adjustment unit 64 adjusts motions in a motion map by using the non-increasing function illustrated in FIG. 5B. When the non-increasing function illustrated in FIG. 5B is used, motions do not decrease through weighting when the total motion is lower than or equal to a predetermined value. Accordingly, when the non-increasing function illustrated in FIG. 5B is used, motions in a motion map are not reduced when signal changes corresponding to movement that does not derive from the movement of the ultrasound probe 1 is detected in the form of motions. Here, movement that does not derive from the movement of the ultrasound probe 1 may be, for example, movement of the puncture needle or movement inside the examination subject's body brought about by breathing, pulsation, etc., of the examination subject.

Here, note that non-increasing functions other than those illustrated in FIGS. 5A and 5B may be used in the adjustment of motions in a motion map. However, the non-increasing function to be used in the adjustment of motions needs to satisfy the three following conditions: (i) when the total motion (motion of the ultrasound probe 1) is small to an extent that it can be regarded that movement of the ultrasound probe 1 has not occurred, the motions are decreased by a small amount and (ii) when the total motion (motion of the ultrasound probe 1) is great to an extent that it can be regarded that movement of the ultrasound probe 1 has occurred, the motions are decreased by a great amount.

Alternatively, a modification may be made such that the ultrasound probe 1 is provided with a sensor that detects position of the ultrasound probe 1 or an angle sensor that detects orientation of the ultrasound probe 1, the movement of the ultrasound probe 1 is detected by using such sensors, and the adjustment of motions is performed such that the greater the movement of the ultrasound probe 1, the smaller the motions after the adjustment.

(3) In embodiment 1, modification of embodiment 1, and embodiment 2, the motion screening unit 63 acquires a motion map from the motion calculation unit 62 and acquires a B-mode image for the latest frame from the B-mode image acquisition unit 5, and provides weights to the motion map based on the luminance values of the B-mode image signal. However, the motion screening unit 63 need not screen motions in a motion map in such a manner. For example, a modification may be made such that the motion screening unit 63 provides weight to pixel areas in a motion map based on luminance values of the pixel areas by using a non-increasing function. Alternatively, for example, a modification may be made such that the motion screening unit 63 performs screening such that a pixel area whose luminance value is smaller than a predetermine value has a motion of zero after the screening. By performing screening in such a manner, motions in a motion map are screened such that only motions of pixel areas having high luminance values remain after the screening.

(4) In embodiment 1, modification of embodiment 1, and embodiment 2, the motion screening unit 63 performs the screening of motions and the motion adjustment unit 64 performs the adjustment of motions in the process of generating a first motion map. However, screening and adjustment of motions need not be performed in such a manner. For example, a modification may be made such that the screening and the adjustment of motions are performed with respect to a third motion map generated by the motion holding unit 66 or the alpha blending unit 166. Alternatively, for example, a modification may be made such that, in place of such screening and adjustment of motions, screening of emphasis is performed with respect to an emphasis map generated by the emphasis allocation unit 68, and adjusting of emphasis is performed by using a total emphasis in the emphasis map.

(5) In embodiments 1 and 2, the motion attenuation unit 67 attenuates motions in a third motion map, the motion holding unit 66 stores, as a second motion map, the third motion map whose motions have been attenuated to a storage medium, and the second motion map stored in the storage medium is used in the generation of a third motion map for a subsequent frame. However, the holding/storing of the second motion map need not be performed in such a manner. For example, a modification may be made such that (i) the process of attenuating motions in a third motion map created for a given frame and (ii) the process of storing and reading a motion map for processing a subsequent frame are performed in the opposite order. That is, for example, the motion holding unit 66 may store a third motion map for a given frame as-is in a storage medium, before the motion attenuation unit 67, when acquiring a first motion map for a subsequent frame, reads the third motion map for the previous frame stored in the storage medium, performs attenuation of motions, and outputs the third motion map whose motions have been attenuated as a second motion map for the subsequent frame to the motion holding unit 66.

Alternatively, for example, a modification may be made such that the motion attenuation unit 67, and not the motion holding unit 66, has a storage medium, and the motion attenuation unit 67 stores the third motion map whose motions have been attenuated as the second motion map. Alternatively, for example, a modification may be made such that the motion attenuation unit 67 includes a delay circuit capable of generating a delay corresponding to one frame, and the motion attenuation unit 67, at a time point later by a time period corresponding to one frame from the acquisition of the third motion map from the motion holding unit 66, outputs the third motion map whose motions have been attenuated to the motion holding unit 66 as the second motion map. When making such a modification, the motion map computation unit 65 is implementable without the use of a storage medium.

(6) In embodiments 1 and 2, the motion holding unit 66, for each pixel, determines the greater one of a motion in the first motion map and a motion in the second motion map, and generates the third motion map by using the greater motions so determined. However, the generation of the third motion map need not be performed in such a manner. For example, a modification may be made such that the motion holding unit 66 generates the third motion map by performing linear combination of the motions in the first motion map and the motions in the second motion map. That is, given $V_1$ denoting the motion of a pixel at a given set of coordinates in the first motion map, $V_2$ denoting the motion of a pixel at the same set of coordinates in the second motion map, and $V_3$ denoting the motion of a pixel at the same set of coordinates in the third motion map, $V_1$, $V_2$, and $V_3$ satisfy: $V_3 = \beta_1 \times V_1 + \beta_2 \times V_2$. In this expression, when for example $\beta_2$ equals one and $\beta_1$ is a value obtained by subtracting the attenuation factor of the motion attenuation unit 67 from one, the processing by the motion holding unit 66 becomes equivalent to the alpha blending described above. However, the values for $\beta_1$ and $\beta_2$ are not limited to such values, and any value greater than zero and no greater than one may be set to $\beta_1$ and $\beta_2$.

(7) In embodiment 1, modification of embodiment 1, and embodiment 2, the motion calculation unit 62 calculates, as a motion for a given pixel area of a motion map, the difference between the squares of the luminance values of the pixel area in two B-mode images. However, the calculation of the motions need not be performed in such a manner. For example, a modification may be made such that motions are calculated by using a predetermined lookup table. Alternatively, for example, a modification may be made such that a distance between corresponding points in two B-mode images (i.e., the magnitude of a motion vector) is determined as a motion.

(8) In embodiment 1, modification of embodiment 1, and embodiment 2, the configuration of the parameters "intensity", "image lag", and "emphasize with color" is received in the beginning of processing, and when such parameters are not configured, values preset to the ultrasound diagnostic device are used. However, the setting of such parameters need not be performed in such a manner. For example, a modification may be made such that at any point following reception of a predetermined input operation via the controller 9, the configuration of the parameters can be made. Alternatively, a modification may be made such that when an operator does not perform any configuration with respect to one or more of the parameters, the values previously set to the parameters are used.

(9) In embodiment 2, the generation of the third motion map is performed in the same way as in embodiment 1. Alternatively, a modification may be made to embodiment 2 such that the third motion map is generated through alpha blending, which is similar to the generation of the third motion map in the modification of embodiment 1.

(10) In embodiment 2, emphasis adding is performed with respect to a frame echo signal. However, the emphasis-adding need not be performed with respect to a frame echo signal in embodiment 2. For example, a modification may be made such that emphasis-adding is performed with respect to reception signals obtained based on echo signals and a B-mode image signal is generated by performing coordinate conversion on the emphasis-added reception signals to obtain a signal based on an orthogonal coordinate system. Here, the reception signals are signals obtained by performing processing such as envelope detection and logarithmic compression with respect to echo signals to convert the echo signals into luminance signals. Alternatively, for example, a modification may be made such that emphasis-adding is performed with respect to a reception signal obtained based on echo signals and a B-mode image signal is generated by performing processing such as envelope detection and logarithmic compression with respect to the emphasis-added reception signal to convert the emphasis-added reception signal into a luminance signal. Here, the reception signal is a signal obtained by performing coordinate conversion on echo signals to obtain a signal based on an orthogonal coordinate system. That is, the emphasis-adding may be performed with respect to a reception signal at any point before the reception signal, which originally is a frame echo signal, is converted into a B-mode image signal, and the emphasis-added reception signal may be converted into a B-mode image signal.

Alternatively, a modification may be made such that a B-mode image signal is generated after an emphasis map for a frame echo signal is generated, and the emphasis-adding is performed with respect to the B-mode image so generated by using the emphasis map. When making such a modification, emphasis-adding, such as the changing of color tone and/or the overlaying of icons, can be readily performed with respect to B-mode image signals. Alternatively, a modification may be made such that an emphasis map is generated with respect to a reception signal at any stage, and the emphasis-adding by using the emphasis map is performed with respect to a B-mode image signal after the B-mode image signal is obtained through conversion of the reception signal.

(11) In embodiment 1, modification of embodiment 1, and embodiment 2, one pixel area corresponds to one pixel. However, each pixel area need not correspond to one pixel. For example, a modification may be made such that one pixel area is an area composed of two-by-two pixels, i.e., a total of four pixels. Providing pixels areas with such a size reduces the amount of processing required in the generation and updating of motion maps, the creation of an emphasis map, and the emphasis adding.

(12) In embodiment 1, modification of embodiment 1, and embodiment 2, the ultrasound probe 1, the controller 9, and the display 10 are external devices connected to the ultrasound diagnostic device. However, the ultrasound diagnostic device may have a different structure. For example, a modification may be made such that the ultrasound diagnostic device includes at least one of the ultrasound probe 1, the controller 9, and the display 10. Alternatively, a modification may be made such that the ultrasound diagnostic device does not include the ultrasound probe 1, the ultrasound transmission/reception unit 2, the transmission/reception control unit 3, nor the B-mode image generation unit 4, and directly acquires B-mode images from an external source.

(13) All structural elements of the ultrasound diagnostic devices pertaining to the embodiments and the modifications above are implemented by using an integrated circuit of one. Alternatively, some of the structural elements of the ultrasound diagnostic devices may be implemented by using an integrated circuit of one or multiple chips, by using a computer program, or in any other form. For example, the emphasis map generation unit may be implemented by using one chip, and the rest of the structural elements, such as the display controller, may be implemented by using another chip.

When implementing the ultrasound diagnostic device by using an integrated circuit, a large scale integration (LSI) is typically used. Here, an LSI may variously be referred to as an IC, system LSI, super LSI, or ultra LSI, depending on the degree of integration.

Further, circuit integration need not be achieved in the form of an LSI, and may be achieved by a dedicated circuit or a general-purpose processor. That is, the circuit integration may be achieved by using field programmable gate arrays (FPGAs) or reconfigurable processors. An FPGA is an LSI that can be programmed after the manufacturing thereof. A reconfigurable processor is an LSI having internal circuits cells whose connection and settings can be reconfigured after the manufacturing thereof.

Furthermore, if circuit integration technology to replace LSI arises due to progress in semiconductor technology and other derivative technologies, such technology may of course be used to perform integration of function blocks.

Further, the ultrasound diagnostic device pertaining to the embodiments and the modifications above may be implemented by using a combination of a program stored on a storage medium and a computer including a memory and a programmable device, such as a central processing unit (CPU) and/or a graphics processing unit (GPU), that reads and executes the program. Here, the storage medium may be any kind of storage medium, such as a memory card, CD-ROM, etc. Further, the ultrasound diagnostic device pertaining to the embodiments and the modifications may be implemented by using a program downloadable via a network and a computer capable of downloading the program via the network and executing the program.

(12) The embodiments described above merely illustrate preferred examples of embodiment of the present disclosure. The numerical values, shapes, materials, structural elements, the arrangement and connection of the structural elements, steps, the processing order of the steps, etc., shown in the embodiments are mere examples, and therefore do not limit the spirit and scope of the present disclosure. Also note that among the structural elements and steps described in the embodiments, structural elements and steps that are not included in the independent claims, which indicate a general concept of the present disclosure, are optional structural elements and steps that are included in order to explain preferred embodiments of the present disclosure.

In order to facilitate understanding, structural elements are not necessarily illustrated to scale in the drawings referred to in the embodiments. The present disclosure is of course not limited by contents of the embodiments and various modifications may be made so long as such modifications do not deviate from the intended scope of the present disclosure.

In an ultrasound diagnostic apparatus, circuit components, leads, and the like are mounted on a substrate. Electrical wiring and circuits can be implemented in various different configurations based on common knowledge in the relevant technical field. However, as such configurations are not directly relevant to explanation of the present disclosure, explanation thereof is omitted. Also note that each of the drawings is a schematic drawing and thus does not necessarily provide a strictly accurate illustration of the matter included therein.

Although the technology pertaining to the present disclosure has been fully described by way of examples with reference to the accompanying drawings, it is to be noted that various changes and modifications will be apparent to those skilled in the art. Therefore, unless such changes and modifications depart from the scope of the present disclosure, they should be construed as being included therein.

What is claimed is:

1. An ultrasound diagnostic device that transmits ultrasound waves towards a subject via an ultrasound probe and acquires frame signals generated at different time points by receiving ultrasound waves reflected by the subject via the ultrasound probe, the ultrasound diagnostic device comprising:

an ultrasound image processing circuit that includes:
a signal acquirer that acquires, via the ultrasound probe, the frame signals;
a map generator that generates, by using the acquired frame signals, a first motion map which is a motion map composed of a plurality of pixel areas which make up an entire frame area of the acquired frame signals, and which indicates a motion in each of the plurality of pixel areas in the entire frame area, the motion indicating an inter-frame signal change and calculated from corresponding pixel areas of the acquired frame signals;
a weight provider that provides a weight to each motion in the first motion map, and outputs the first motion map whose motions have been weighted, wherein the weight provider provides the weight to each motion in the first motion map by comparing, to a predetermined value, a luminance value of a pixel area corresponding to each motion in one of the acquired frame signals which is used to calculate the first motion map, and providing the weight in accordance with the luminance value of the corresponding pixel area such that the weight increases in accordance with an increase in luminance value of the corresponding pixel area in said one of the acquired frame signals, wherein when the luminance value of the corresponding pixel area is lower than the predetermined value, the weight provider provides the weight to the motion in the first motion map by using zero as a weighting coefficient, and when the luminance value of the corresponding pixel area is greater than or equal to the predetermined value, the weight provider provides the weight to the motion in the first motion map by using a number greater than zero as a weighting coefficient;
a map calculator that holds a second motion map and creates a third motion map by performing a calculation using motions in the first motion map output by the weight provider and the second motion map, wherein each of the second motion map and the third motion map is a motion map composed of a plurality of pixel areas which make up an entire frame area of the acquired frame signals, and which indicates a motion in each of the plurality of pixel areas in the entire frame area;
an emphasis adder that adds emphasis to at least one of the acquired frame signals by using the third motion map and generates an ultrasound image from said at least one of the acquired frame signals to which emphasis has been added; and
a display controller that controls a display to display the generated ultrasound image, wherein, after the third motion map is calculated using the motions in the first motion map and the second motion map, the map calculator holds the created third motion map as a new second motion map for performing a subsequent calculation to create a new third motion map.

2. The ultrasound diagnostic device of claim 1, wherein in the creation of the third motion map, the map calculator sets, as a motion for each pixel area of the third motion map, a greater one of (i) a value obtained by attenuating a motion of a corresponding pixel area in the second motion map based on a predetermined attenuation factor and (ii) a motion of a corresponding pixel in the first motion map.

3. The ultrasound diagnostic device of claim 2, wherein the predetermined attenuation factor is set according to a frame rate of the acquired frame signals.

4. The ultrasound diagnostic device of claim 2, further comprising a controller for receiving input of the predetermined attenuation factor.

5. The ultrasound diagnostic device of claim 1, wherein the calculation using motions comprises alpha-blending the second motion map and the first motion map.

6. The ultrasound diagnostic device of claim 5, wherein an alpha value used in the alpha blending is set according to a frame rate of the acquired frame signals.

7. The ultrasound diagnostic device of claim 5, further comprising a controller for receiving input of an alpha value to be used in the alpha blending.

8. The ultrasound diagnostic device of claim 1, wherein the ultrasound image processing circuit further includes an emphasis adjuster that, when a movement of the ultrasound probe in a direction along a surface of the subject occurs, detects the movement of the ultrasound probe, adjusts motions in the third motion map based on the detected movement of the ultrasound probe by using a non-increasing function whose input is the movement of the ultrasound probe and whose output is an amount of motion to be adjusted, and outputs the third motion map, whose motions have been adjusted, to the emphasis adder.

9. The ultrasound diagnostic device of claim 8, wherein the emphasis adjuster calculates a signal change in the acquired frame signals indicating the movement of the ultrasound probe by using the first motion map, and the emphasis adjuster adjusts the motions in the third motion map based on the calculated signal change.

10. The ultrasound diagnostic device of claim 8, wherein:
the ultrasound probe includes a sensor that detects either a position of the ultrasound probe or an orientation of the ultrasound probe with respect to the subject, and
the emphasis adjuster detects a value output by the sensor as a signal change indicating the movement of the ultrasound probe, and the emphasis adjuster adjusts the motions in the third motion map based on the detected signal change.

11. The ultrasound diagnostic device of claim 1, wherein the ultrasound image processing circuit further includes:
an emphasis adjuster that, when a movement of the ultrasound probe in a direction along a surface of the subject occurs, detects the movement of the ultrasound probe, adjusts the motions in the first motion map based on the detected movement of the ultrasound probe by using a non-increasing function whose input is the movement of the ultrasound probe and whose output is an amount of motion to be adjusted, and outputs the first motion map, whose motions have been adjusted, to the map calculator.

12. The ultrasound diagnostic device of claim 11, wherein the emphasis adjuster calculates a signal change in the acquired frame signals indicating the movement of the ultrasound probe by using the first motion map, and the emphasis adjuster adjusts the motions in the third motion map based on the calculated signal change.

13. The ultrasound diagnostic device of claim 11, wherein:
the ultrasound probe includes a sensor that detects either a position of the ultrasound probe or an orientation of the ultrasound probe with respect to the subject, and
the emphasis adjuster detects a value output by the sensor as a signal change indicating the movement of the ultrasound probe, and the emphasis adjuster adjusts the motions in the third motion map based on the detected signal change.

14. The ultrasound diagnostic device of claim 1, wherein the emphasis adder changes a pixel value of a pixel area of said at least one of the acquired frame signals based on a motion at a corresponding pixel area in the third motion map by using a non-decreasing function whose input is the motion at the corresponding pixel area in the third motion map and whose output is an amount of emphasis to be added to the pixel area in said at least one of the acquired frame signals.

15. The ultrasound diagnostic device of claim 1, wherein the emphasis adder adds emphasis to one or more pixel areas of said at least one of the acquired frame signals corresponding to one or more pixel areas in the third motion map having a motion greater than a predetermined threshold value.

16. The ultrasound diagnostic device of claim 1, wherein the emphasis adder adds emphasis to one or more pixel areas of said at least one of the acquired frame signals corresponding to one or more pixel areas in the third motion map having a motion greater than a predetermined threshold value, the adding of emphasis performed by overlaying an icon and changing a pixel value.

17. The ultrasound diagnostic device of claim 1, wherein the emphasis adder adds emphasis to one pixel area of said at least one of the acquired frame signals corresponding to one pixel area in the third motion map having a greatest motion, the adding of emphasis performed by overlaying an icon and changing a pixel value.

18. The ultrasound diagnostic device of claim 1, further comprising a storage medium for storing the second motion map,
wherein the map calculator holds the second motion map by writing the second motion map to the storage medium.

19. An ultrasound image processing method for an ultrasound diagnostic device that transmits ultrasound waves towards a subject via an ultrasound probe and acquires frame signals generated at different time points by receiving ultrasound waves reflected by the subject via the ultrasound probe, the ultrasound image processing method comprising:
acquiring, via the ultrasound probe, the frame signals;
generating, by using the acquired frame signals, a first motion map which is a motion map composed of a plurality of pixel areas which make up an entire frame area of the acquired frame signals, and which indicates a motion in each of the plurality of pixel areas in the entire frame area, the motion indicating an inter-frame signal change and calculated from corresponding pixel areas of the acquired frame signals;
providing a weight to each motion in the first motion map, and outputting the first motion map whose motions have been weighted, wherein the weight is provided to each motion in the first motion map by comparing, to a predetermined value, a luminance value of a pixel area corresponding to each motion in one of the acquired frame signals which is used to calculate the first motion map, and providing the weight in accordance with the luminance value of the corresponding pixel area such that the weight increases in accordance with an increase in luminance value of the corresponding pixel area in said one of the acquired frame signals, wherein when the luminance value of the corresponding pixel area is lower than the predetermined value, the weight is provided to the motion in the first motion map by using zero as a weighting coefficient, and when the luminance value of the corresponding pixel area is greater than or equal to the predetermined value, the weight is provided to the motion in the first motion map by using a number greater than zero as a weighting coefficient;

holding a second motion map and creating a third motion map by performing a calculation using motions in the output first motion map whose motions have been weighted and the second motion map, wherein each of the second motion map and the third motion map is a motion map composed of a plurality of pixel areas which make up an entire frame area of the acquired frame signals, and which indicates a motion in each of the plurality of pixel areas in the entire frame area;

adding emphasis to at least one of the acquired frame signals by using the third motion map and generating an ultrasound image from said at least one of the acquired frame signals to which emphasis has been added; and controlling a display to display the generated ultrasound image, wherein:

after the third motion map is calculated using the motions in the first motion map and the second motion map, the created third motion map is held as a new second motion map for performing a subsequent calculation to create a new third motion map.

20. A non-transitory computer-readable recording medium storing thereon a program that is executable by a processor of an ultrasound diagnostic device that transmits ultrasound waves towards a subject via an ultrasound probe and acquires frame signals generated at different time points by receiving ultrasound waves reflected by the subject via the ultrasound probe, the program being executable by the processor to cause the processor to perform functions comprising:

acquiring, via the ultrasound probe, the frame signals;

generating, by using the acquired frame signals, a first motion map which is a motion map composed of a plurality of pixel areas which make up an entire frame area of the acquired frame signals, and which indicates a motion in each of the plurality of pixel areas in the entire frame area, the motion indicating an inter-frame signal change and calculated from corresponding pixel areas of the acquired frame signals;

providing a weight to each motion in the first motion map, and outputting the first motion map whose motions have been weighted, wherein the weight is provided to each motion in the first motion map by comparing, to a predetermined value, a luminance value of a pixel area corresponding to each motion in one of the acquired frame signals which is used to calculate the first motion map, and providing the weight in accordance with the luminance value of the corresponding pixel area such that the weight increases in accordance with an increase in luminance value of the corresponding pixel area in said one of the acquired frame signals, wherein when the luminance value of the corresponding pixel area is lower than the predetermined value, the weight is provided to the motion in the first motion map by using zero as a weighting coefficient, and when the luminance value of the corresponding pixel area is greater than or equal to the predetermined value, the weight is provided to the motion in the first motion map by using a number greater than zero as a weighting coefficient;

holding a second motion map and creating a third motion map by performing a calculation using motions in the output first motion map whose motions have been weighted and the second motion map, wherein each of the second motion map and the third motion map is a motion map composed of a plurality of pixel areas which make up an entire frame area of the acquired frame signals, and which indicates a motion in each of the plurality of pixel areas in the entire frame area;

adding emphasis to at least one of the acquired frame signals by using the third motion map and generating an ultrasound image from said at least one of the acquired frame signals to which emphasis has been added; and controlling a display to display the generated ultrasound image, wherein after the third motion map is calculated using the motions in the first motion map and the second motion map, the created third motion map is held as a new second motion map for performing a subsequent calculation to create a new third motion map.

21. An ultrasound diagnostic device that transmits ultrasound waves towards a subject via an ultrasound probe and acquires frame signals generated at different time points by receiving ultrasound waves reflected by the subject via the ultrasound probe, the ultrasound diagnostic device comprising:

an ultrasound image processing circuit that is configured to:

acquire, via the ultrasound probe, the frame signals;

generate, by using the acquired frame signals, a first motion map which is a motion map composed of a plurality of pixel areas which make up an entire frame area of the acquired frame signals, and which indicates a motion in each of the plurality of pixel areas in the entire frame area, the motion indicating an inter-frame signal change and calculated from corresponding pixel areas of the acquired frame signals;

provide a weight to each motion in the first motion map, and output the first motion map whose motions have been weighted, wherein the ultrasound image processing circuit provides the weight to each motion in the first motion map by comparing, to a predetermined value, a luminance value of a pixel area corresponding to each motion in one of the acquired frame signals which is used to calculate the first motion map, and providing the weight in accordance with the luminance value of the corresponding pixel area such that the weight increases in accordance with an increase in luminance value of the corresponding pixel area in said one of the acquired frame signals, wherein when the luminance value of the corresponding pixel area is lower than the predetermined value, the ultrasound image processing circuit provides the weight to the motion in the first motion map by using zero as a weighting coefficient, and when the luminance value of the corresponding pixel area is greater than or equal to the predetermined value, the ultrasound image processing circuit provides the weight to the motion in the first motion map by using a number greater than zero as a weighting coefficient;

hold a second motion map and create a third motion map by performing a calculation using motions in the first motion map and the held second motion map, wherein each of the second motion map and the third motion map is a motion map composed of a plurality of pixel areas which make up an entire frame area of the acquired frame signals, and which indicates a motion in each of the plurality of pixel areas in the entire frame area, wherein after the third motion map is calculated using the motions in the first motion map and the second motion map, the ultrasound image processing circuit holds the created third motion map as a new second motion map for performing a subsequent calculation to create a new third motion map;

add emphasis to at least one of the acquired frame signals by using the third motion map;

generate an ultrasound image from said at least one of the frame signals to which emphasis has been added; and control a display to display the generated ultrasound image.

* * * * *